US010675280B2

(12) United States Patent
Borsini et al.

(10) Patent No.: US 10,675,280 B2
(45) Date of Patent: *Jun. 9, 2020

(54) TREATING SEXUAL DESIRE DISORDERS WITH FLIBANSERIN

(71) Applicant: Sprout Pharmaceuticals, Inc., Raleigh, NC (US)

(72) Inventors: Franco Borsini, Baden Württemberg (DE); Kenneth Robert Evans, Toronto (CA)

(73) Assignee: Sprout Pharmaceuticals, Inc., Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/412,009

(22) Filed: May 14, 2019

(65) Prior Publication Data

US 2019/0262336 A1 Aug. 29, 2019

Related U.S. Application Data

(63) Continuation of application No. 16/125,883, filed on Sep. 10, 2018, now Pat. No. 10,307,420, which is a continuation of application No. 15/694,317, filed on Sep. 1, 2017, now Pat. No. 10,098,876, which is a continuation of application No. 15/270,167, filed on Sep. 20, 2016, now Pat. No. 9,782,403, which is a continuation of application No. 14/640,055, filed on Mar. 6, 2015, now Pat. No. 9,468,639, which is a continuation of application No. 14/269,373, filed on May 5, 2014, now abandoned, which is a continuation of application No. 13/920,354, filed on Jun. 18, 2013, now abandoned, which is a continuation of application No. 13/551,036, filed on Jul. 17, 2012, now abandoned, which is a continuation of application No. 11/524,268, filed on Sep. 21, 2006, now Pat. No. 8,227,471, which is a continuation of application No. 10/272,603, filed on Oct. 16, 2002, now Pat. No. 7,151,103.

(60) Provisional application No. 60/348,911, filed on Oct. 23, 2001.

(30) Foreign Application Priority Data

Oct. 20, 2001 (EP) .................................. 01125020

(51) Int. Cl.
*A61K 31/496* (2006.01)

(52) U.S. Cl.
CPC .................................. *A61K 31/496* (2013.01)

(58) Field of Classification Search
CPC .................................................. A61K 31/496
See application file for complete search history.

(56) References Cited

U.S. PATENT DOCUMENTS

| | | |
|---|---|---|
| 3,096,248 A | 7/1963 | Rudzki |
| 3,406,178 A | 10/1968 | Crocker et al. |
| 3,472,854 A | 10/1969 | Archer |
| 4,200,641 A | 4/1980 | Vandenberk et al. |
| 4,367,217 A | 1/1983 | Gruber et al. |
| 4,438,091 A | 3/1984 | Gruber et al. |
| 4,737,500 A | 4/1988 | Sorg |
| 4,792,452 A | 12/1988 | Howard et al. |
| 4,797,399 A | 1/1989 | Ueda et al. |
| 4,859,692 A | 8/1989 | Bernstein et al. |
| 4,886,803 A | 12/1989 | Sueda et al. |
| 4,940,793 A | 7/1990 | Botre et al. |
| 4,954,503 A | 9/1990 | Strupczewski et al. |
| 4,968,508 A | 11/1990 | Oren et al. |
| 5,002,948 A | 3/1991 | Perregaard et al. |
| 5,036,088 A | 7/1991 | Kitaura et al. |
| 5,225,417 A | 7/1993 | Dappen et al. |
| 5,281,585 A | 1/1994 | Duggan et al. |
| 5,405,642 A | 4/1995 | Gilis |
| 5,407,686 A | 4/1995 | Patel et al. |
| 5,434,156 A | 7/1995 | Bjork et al. |
| 5,482,948 A | 1/1996 | Soyka et al. |
| 5,492,907 A | 2/1996 | Pickar et al. |
| 5,552,412 A | 9/1996 | Cameron et al. |
| 5,576,290 A | 11/1996 | Hadley |
| 5,576,318 A | 11/1996 | Bietti .................. C07D 235/26 514/252.19 |
| 5,591,743 A | 1/1997 | Patoiseau et al. |
| 5,854,290 A | 12/1998 | Arnsten et al. |
| 5,883,094 A | 3/1999 | Fliri et al. |
| 5,916,916 A | 6/1999 | Hauser et al. |
| 5,929,054 A | 7/1999 | Baker et al. |
| 5,977,106 A | 11/1999 | Patoiseau et al. |
| 6,051,555 A | 4/2000 | Hadley |
| 6,068,846 A | 5/2000 | Cho et al. |
| 6,083,947 A | 7/2000 | Granger ................. A61K 31/00 514/249 |

(Continued)

FOREIGN PATENT DOCUMENTS

| | | |
|---|---|---|
| AU | 2006311036 B2 | 1/2013 |
| AU | 2006311038 B2 | 1/2013 |

(Continued)

OTHER PUBLICATIONS

U.S. Appl. No. 08/039,002, filed Mar. 25, 1993, Bietti.
U.S. Appl. No. 11/956,949, filed Dec. 14, 2007, Lewis-D'Agostino, et al.
U.S. Appl. No. 12/390,665, filed Feb. 23, 2009, Wunderlich, et al.
U.S. Appl. No. 12/532,269, filed Dec. 14, 2009, Boeck, et al.
U.S. Appl. No. 12/675,231, filed Feb. 25, 2010, Hanes, et al.
Alexander et al., J. of Am. Acad. of Nurse Practitioners, 2007, 19-152-163.
Borsini et al., Pharmacology of Flibanserin, CNS Drug Reviews, 2002; 8(2):117-142.

(Continued)

*Primary Examiner* — Trevor Love
(74) *Attorney, Agent, or Firm* — Womble Bond Dickinson (US) LLP

(57) ABSTRACT

The invention relates to the use of flibanserin, or a pharmaceutically acceptable acid addition salt thereof, for the treatment of disorders of sexual desire.

25 Claims, No Drawings

(56) References Cited

U.S. PATENT DOCUMENTS

| | | | |
|---|---|---|---|
| 6,165,513 A | 12/2000 | Dansereau et al. | |
| 6,187,340 B1 | 2/2001 | Fukuta et al. | |
| 6,281,218 B1 | 8/2001 | Cereda et al. | |
| 6,284,757 B1 | 9/2001 | Sanner | |
| 6,346,548 B1 | 2/2002 | Miller et al. | |
| 6,426,087 B1 | 7/2002 | Saslawski | |
| 6,482,841 B1 | 11/2002 | Letelier et al. | |
| 6,521,623 B1 | 2/2003 | Cereda et al. | 514/252.19 |
| 6,586,435 B2 | 7/2003 | Cereda et al. | |
| 6,627,646 B2 | 9/2003 | Bakale et al. | |
| 6,680,071 B1 | 1/2004 | Johnson et al. | |
| 7,151,103 B2 | 12/2006 | Borsini | A61K 31/496 514/252.19 |
| 7,183,410 B2 | 2/2007 | Bombarda | C07D 235/26 544/295 |
| 7,241,805 B2 | 7/2007 | Oberegger et al. | |
| 7,420,057 B2 | 9/2008 | Bombarda et al. | |
| 7,923,449 B2 | 4/2011 | Ceci | |
| 7,973,043 B2 | 7/2011 | Migaly | |
| 8,030,314 B2 | 10/2011 | Beck | |
| 8,227,471 B2 | 7/2012 | Borsini | A61K 31/496 514/254.06 |
| 8,227,476 B2 | 7/2012 | Ceci et al. | |
| 8,545,886 B2 | 10/2013 | Eisenreich et al. | |
| 8,658,207 B2 | 2/2014 | Eisenreich et al. | |
| 8,722,682 B2 | 5/2014 | Volz et al. | |
| 8,785,458 B2 | 7/2014 | Ceci et al. | |
| 2002/0001397 A1 | 1/2002 | Ishikawa et al. | |
| 2002/0010216 A1 | 1/2002 | Rogosky et al. | |
| 2002/0052370 A1 | 5/2002 | Barber et al. | |
| 2002/0091115 A1 | 7/2002 | Dyatkin et al. | |
| 2002/0103208 A1 | 8/2002 | Cereda et al. | |
| 2002/0151543 A1 | 10/2002 | Barberich et al. | |
| 2002/0160042 A1 | 10/2002 | Petereit et al. | |
| 2003/0027823 A1 | 2/2003 | Cereda et al. | |
| 2003/0055070 A1 | 3/2003 | Harrison et al. | |
| 2003/0060475 A1 | 3/2003 | Borsini | |
| 2003/0083228 A1 | 5/2003 | Carpino et al. | |
| 2003/0104980 A1 | 6/2003 | Borsini et al. | |
| 2003/0119850 A1 | 6/2003 | Bombarda et al. | 514/254.06 |
| 2004/0023948 A1 | 2/2004 | Green et al. | |
| 2004/0048877 A1 | 3/2004 | Friedl et al. | 514/254.06 |
| 2004/0116532 A1 | 6/2004 | Heacock et al. | |
| 2004/0132697 A1 | 7/2004 | Thurlow et al. | |
| 2004/0147581 A1 | 7/2004 | Taylor | |
| 2004/0180904 A1 | 9/2004 | Beck | |
| 2004/0193452 A1 | 9/2004 | Berman | |
| 2004/0198706 A1 | 10/2004 | Carrara et al. | |
| 2004/0235861 A1 | 11/2004 | Borsini | |
| 2004/0258749 A1 | 12/2004 | Guldner et al. | |
| 2005/0004105 A1 | 1/2005 | Leahy et al. | |
| 2005/0037983 A1 | 2/2005 | Dinan et al. | |
| 2005/0065158 A1 | 3/2005 | Naylor et al. | |
| 2005/0090550 A1 | 4/2005 | Barrett | |
| 2005/0095293 A1 | 5/2005 | Brauns et al. | |
| 2005/0159430 A1 | 7/2005 | Bombarda et al. | |
| 2005/0239798 A1 | 10/2005 | Pyke | |
| 2005/0245539 A1 | 11/2005 | Mendla et al. | |
| 2006/0014757 A1 | 1/2006 | Pyke | |
| 2006/0025420 A1 | 2/2006 | Brauns et al. | |
| 2006/0052391 A1 | 3/2006 | Dolsten | |
| 2006/0084700 A1 | 4/2006 | Michel | |
| 2006/0160822 A1 | 7/2006 | Borsini | |
| 2006/0199805 A1 | 9/2006 | Pyke et al. | |
| 2006/0204486 A1 | 9/2006 | Pyke et al. | |
| 2006/0211685 A1 | 9/2006 | Pyke et al. | |
| 2006/0252773 A1 | 11/2006 | Ceci et al. | |
| 2006/0258640 A1 | 11/2006 | Ceci et al. | |
| 2006/0264511 A1 | 11/2006 | Pyke | |
| 2006/0264512 A1 | 11/2006 | Pyke | |
| 2007/0032654 A1 | 2/2007 | Bombarda et al. | |
| 2007/0032655 A1 | 2/2007 | Bombarda et al. | |
| 2007/0072872 A1 | 3/2007 | Borsini | |
| 2007/0105869 A1 | 5/2007 | Pollentier et al. | |
| 2007/0123540 A1 | 5/2007 | Ceci | |
| 2007/0196473 A1 | 8/2007 | Friedl et al. | |
| 2007/0265276 A1 | 11/2007 | Pollentier | |
| 2008/0038346 A1 | 2/2008 | Eisenreich et al. | |
| 2008/0038347 A1 | 2/2008 | Eisenreich et al. | |
| 2008/0069873 A1 | 3/2008 | Pearnchob et al. | |
| 2008/0103155 A1 | 5/2008 | Mendla et al. | |
| 2008/0119482 A1 | 5/2008 | Dolsten | |
| 2008/0242678 A1 | 10/2008 | Ceci et al. | |
| 2008/0242679 A1 | 10/2008 | Ceci | |
| 2008/0275082 A1 | 11/2008 | Brum et al. | |
| 2009/0022797 A1 | 1/2009 | Rossi et al. | |
| 2009/0023712 A1 | 1/2009 | Ferger et al. | |
| 2009/0054458 A1 | 2/2009 | Bombarda et al. | |
| 2009/0176698 A1 | 7/2009 | Baiker et al. | |
| 2009/0239881 A1 | 9/2009 | Becker | |
| 2009/0247546 A1 | 10/2009 | Ceci et al. | |
| 2009/0312242 A1 | 12/2009 | Castro et al. | |
| 2009/0318469 A1 | 12/2009 | Pyke et al. | |
| 2011/0015207 A1 | 1/2011 | Volz et al. | |
| 2011/0136825 A1 | 6/2011 | Hanes et al. | |
| 2012/0035185 A1 | 2/2012 | Borsini | |
| 2012/0122883 A1 | 5/2012 | Mazurek et al. | |
| 2012/0270883 A1 | 10/2012 | Bombarda et al. | |
| 2013/0079355 A1 | 3/2013 | Ceci et al. | |
| 2013/0079356 A1 | 3/2013 | Pyke | |
| 2013/0096137 A1 | 4/2013 | Borsini | |
| 2013/0172304 A1 | 7/2013 | Boeck | |
| 2013/0203671 A1 | 8/2013 | Castro et al. | |
| 2013/0203766 A1 | 8/2013 | Mendla et al. | |

FOREIGN PATENT DOCUMENTS

| | | |
|---|---|---|
| AU | 2007247094 B2 | 2/2013 |
| BE | 904945 | 12/1986 |
| BE | 904945 A1 | 12/1986 |
| CA | 2455628 | 2/2003 |
| CA | 2 515 426 C | 1/2012 |
| CA | 2 563 167 C | 4/2013 |
| CL | 1033-1999 | 5/1999 |
| CL | 2394-1999 | 10/1999 |
| CL | 1491-2001 | 6/2001 |
| CL | 2833-2001 | 11/2001 |
| CL | 418-2002 | 3/2002 |
| CL | 911-2005 | 4/2002 |
| CL | 1706-2002 | 7/2002 |
| CL | 1878-2002 | 8/2002 |
| CL | 2389-2002 | 10/2002 |
| CL | 1751-2004 | 7/2004 |
| CN | 1571670 A | 1/2005 |
| CN | 1655789 A | 8/2005 |
| DE | 3620643 | 1/1987 |
| DE | 10209982.0 | 3/2002 |
| DE | 10138273 | 2/2003 |
| EP | 0200322 | 11/1986 |
| EP | 200322 | 11/1986 |
| EP | 0200322 A1 | 11/1986 |
| EP | 376607 | 4/1990 |
| EP | 497985 | 12/1992 |
| EP | 0 526 434 A1 | 2/1993 |
| EP | 526434 | 2/1993 |
| EP | 0547517 A1 | 6/1993 |
| EP | 0705832 | 4/1996 |
| EP | 705832 | 4/1996 |
| EP | 816356 | 1/1998 |
| EP | 0816356 | 1/1998 |
| EP | 0982030 | 3/2000 |
| EP | 982030 | 3/2000 |
| EP | 1 256 343 A1 | 11/2002 |
| EP | 1256343 | 11/2002 |
| EP | 1 285 658 A2 | 2/2003 |
| EP | 1285658 | 2/2003 |
| EP | 1014985 | 5/2003 |
| EP | 1518858 | 3/2005 |
| EP | 1674102 | 6/2006 |
| EP | 1 948 177 B1 | 8/2011 |
| EP | 1 322 622 B1 | 10/2012 |
| GB | 2023594 | 1/1980 |
| GB | 2023594 A | 1/1980 |
| IE | 1992/1340 | 10/1992 |

(56) References Cited

FOREIGN PATENT DOCUMENTS

| | | |
|---|---|---|
| IL | 159151 | 2/2003 |
| IL | 160389 | 2/2004 |
| JP | 58134033 | 8/1983 |
| JP | H8-143476 | 6/1996 |
| RU | 93014306 | 3/1995 |
| WO | WO 1992002215 A1 | 2/1992 |
| WO | WO 92/03167 | 3/1992 |
| WO | WO 92/19606 | 11/1992 |
| WO | WO 93/03016 | 2/1993 |
| WO | WO 95/01965 | 1/1995 |
| WO | WO 1995/19978 A1 | 7/1995 |
| WO | WO 95/034555 | 12/1995 |
| WO | WO 96/05834 | 2/1996 |
| WO | WO 96/16949 | 6/1996 |
| WO | 98/19668 A1 | 5/1998 |
| WO | WO 98/19668 | 5/1998 |
| WO | WO 98/33784 | 8/1998 |
| WO | WO 98/42344 | 10/1998 |
| WO | WO 99/19302 | 4/1999 |
| WO | WO 1999059593 A1 | 5/1999 |
| WO | WO 1999059584 A1 | 11/1999 |
| WO | 99/064002 A1 | 12/1999 |
| WO | WO 00/028993 | 5/2000 |
| WO | WO 200028993 A1 | 5/2000 ........... A61K 31/495 |
| WO | WO 2000024383 A1 | 5/2000 |
| WO | WO 2000/63193 A1 | 10/2000 |
| WO | 00/064441 A2 | 11/2000 |
| WO | WO 00/64441 | 11/2000 |
| WO | WO 2000/67735 A2 | 11/2000 |
| WO | 01/00224 A1 | 1/2001 |
| WO | WO 2001/00224 A1 | 1/2001 |
| WO | WO 01/12170 | 2/2001 |
| WO | 01/21593 A1 | 3/2001 |
| WO | WO 01/021593 | 3/2001 |
| WO | WO 01/21593 A1 | 3/2001 |
| WO | WO 2002000654 A1 | 1/2002 |
| WO | WO 02/24662 | 3/2002 |
| WO | WO 2002041894 A2 | 5/2002 |
| WO | 02/072586 A1 | 9/2002 |
| WO | 02/074288 A2 | 9/2002 |
| WO | WO 2002072586 A1 | 9/2002 |
| WO | WO 02/079143 | 10/2002 |
| WO | 03/007949 A1 | 1/2003 |
| WO | WO 2003/07949 A1 | 1/2003 |
| WO | 03/013539 A1 | 2/2003 |
| WO | 03/014079 A1 | 2/2003 |
| WO | WO 03/011396 | 2/2003 |
| WO | WO 03/013539 | 2/2003 |
| WO | WO 03/014079 | 2/2003 |
| WO | 03/030869 A1 | 4/2003 |
| WO | 03/035072 A1 | 5/2003 |
| WO | WO 03/014079 | 5/2003 |
| WO | WO 03/035072 | 5/2003 |
| WO | 03/074032 A1 | 9/2003 |
| WO | 03/097056 A1 | 11/2003 |
| WO | 03/097058 A1 | 11/2003 |
| WO | WO 03/097058 | 11/2003 |
| WO | 2004/041259 A1 | 5/2004 |
| WO | WO 2004/041259 | 5/2004 |
| WO | WO 2004/045509 | 6/2004 |
| WO | WO 04/069339 | 8/2004 |
| WO | 2005/007166 A1 | 1/2005 |
| WO | WO 2005/007166 | 1/2005 |
| WO | WO 2005007166 A1 | 1/2005 |
| WO | WO 2005/102343 | 3/2005 |
| WO | WO 2005/044238 | 5/2005 |
| WO | 05/087207 A1 | 9/2005 |
| WO | WO 05/087207 | 9/2005 |
| WO | 2005/102342 A1 | 11/2005 |
| WO | 2005/102343 A1 | 11/2005 |
| WO | WO 05/102342 | 11/2005 |
| WO | 2006/019715 A1 | 2/2006 |
| WO | WO 2006/010574 | 2/2006 |
| WO | WO 2006/019715 | 2/2006 |
| WO | 06/024471 A1 | 3/2006 |
| WO | WO 2006/024471 | 3/2006 |
| WO | WO 2006/96434 A2 | 9/2006 |
| WO | WO 2006/096435 | 9/2006 |
| WO | WO 2006/125041 | 11/2006 |
| WO | 2007/014929 A1 | 2/2007 |
| WO | 2007/014939 A1 | 2/2007 |
| WO | WO 07/014929 | 2/2007 |
| WO | WO 07/048803 | 3/2007 |
| WO | WO 2007/022325 | 3/2007 |
| WO | WO 2007/23325 A2 | 3/2007 |
| WO | WO 2007/090091 | 8/2007 |
| WO | WO 03/074032 | 9/2007 |
| WO | 2008/005838 A1 | 1/2008 |
| WO | 2008/006838 A1 | 1/2008 |
| WO | WO 2008/06839 A2 | 1/2008 |
| WO | WO 2008006838 A1 | 1/2008 |
| WO | 2008-019996 A2 | 2/2008 |
| WO | 2008-022932 A2 | 2/2008 |
| WO | WO 2008/22932 A2 | 2/2008 |
| WO | WO 2008019996 A2 | 2/2008 |
| WO | 2008-110890 A2 | 10/2008 |
| WO | 2008-116890 A2 | 10/2008 |
| WO | WO 2008116890 A2 | 10/2008 |

OTHER PUBLICATIONS

CMU Pharmaceutical polymorphism, http://www.andrew.cmu.edu/user/suter/polymorph.html, internet p. 1-3 (2002) obtained Feb. 11, 2009.
U.S. Appl. No. 12/987,388, filed Jan. 10, 2011, Pyke.
Anderson et al., Guidelines for choice of selective serotonin reuptake inhibitor in depressive illness, Adv. Psychia. Treatment, 2001, 7:170-180.
Anonymous, Gel significantly increases sexual-activity in surgically menopausal women, Online, Nov. 1, 2004, XP002455243, Reuieved from the Internet: URL: http/www.newsmedical.net/print_article.asp?id=5960 [retrieved on Oct. 17, 2007] 8 pgs.
Yekimov, Sex toys and devices in sexual dysfunction therapy. , www.mosmedclinic.ru/conf—library/2002/2/130/, 2002, 6 pgs.
Office Action in commonly owned European Patent Application No. 06807537.3; dated Oct. 11, 2013, 14 pages.
Berendsen, "Hot Flushes and Serotonin," Journal of the British Menopause Society, Mar. 2002, pp. 1-5.
Office Action in counterpart European Patent Application No. 09774901.4; dated Aug. 9, 2013, 4 pages.
International Search Report for PCT/EP08/53592 dated Jun. 4, 2009.
Berge et al., Pharmaceutical Salts, J. Pharm Sci., 1977, 66(1): 1-19.
Kumar et al., An oveview of Automated Systems Relevant in Pharmaceutical Salt Screening: Drug Discovery Today, 2007, 12(23-24): 1046-1053.
Stahl et al., Handbook of Phamaceutical Salts: Selection and Use, Helvetica Chem. Acta. 2002, pp. 1-7.
U.S. Appl. No. 13/131,926, filed May 31, 2011, Mazurek et al.
Eriksson, Serotonin reuptake inhibitors for the treatment of pre-menstrual dysphoria, Intl. Clin. Psychopharm, 1999, 14Supp2:S27-S33.
Steiner et al., Seretonin re-uptake inhibitors in the treatment of premenstrual dysphoria: Current status of knowledge, 1997, 1:241-247.
RCE dated Feb. 15, 2011; U.S. Appl. No. 11/837,962, filed Aug. 13, 2007, 2 pgs.
Response to Final Office Action dated Feb. 15, 2011; U.S. Appl. No. 11/837,962, filed Aug. 13, 2007, 15 pgs.
Notice of Allowance dated Feb. 16, 2011; U.S. Appl. No. 12/091,848, filed Apr. 28, 208, 9 pgs.
Advisory Action dated Feb. 17, 2011; U.S. Appl. No. 11/837,957, filed Aug. 13, 2007, 3 pgs.
Notice of Appeal dated Feb. 22, 2011; U.S. Appl. No. 11/745,515, filed May 8, 2007, 1 pgs.
Notice of Appeal dated Feb. 22, 2011; U.S. Appl. No. 11/554,855, filed Oct. 31, 2006, 1 pgs.
Advisory Action dtaed Mar. 2, 2011; U.S. Appl. No. 11/745,515, filed May 8, 2007, 3 pgs.

(56) References Cited

OTHER PUBLICATIONS

Advisory Action dated Mar. 2, 2011; U.S. Appl. No. 11/554,855, filed Oct. 31, 2006, 3 pgs.
RCE dated Mar. 7, 2011; U.S. Appl. No. 11/837,957, filed Aug. 13, 2007, 2 pgs.
Response to Final Office Action dated Mar. 7, 2011; U.S. Appl. No. 11/837,957, filed Aug. 13, 2007, 9 pgs.
Response to Office Action dated Mar. 14, 2011; U.S. Appl. No. 11/097,939, filed Apr. 4, 2005, 20 pgs.
Interview Summary dated Mar. 15, 2011; U.S. Appl. No. 11/097,939, filed Apr. 4, 2005, 4 pgs.
Interview Summary dated Apr. 6, 2011; U.S. Appl. No. 11/997,567, filed Mar. 21, 2008, 3 pgs.
Response/Amendment dated Apr. 12, 2011; U.S. Appl. No. 11/997,567, filed Mar. 21, 2008, 9 pgs.
Final Office Action dated Apr. 19, 2011, U.S. Appl. No. 11/276,551, filed Apr. 4, 2006, 9 pgs.
Response to Office Action dated May 2, 2011; U.S. Appl. No. 12/390,665, filed Feb. 23, 2009, 11 pgs.
Office Action dated May 27, 2011, U.S. Appl. No. 12/170,884, filed Jul. 10, 2008, 6 pgs.
Office Action dated May 31, 2011; U.S. Appl. No. 11/097,939, filed Apr. 4, 2005, 15 pgs.
Final Office Action dated Jun. 16, 2011; U.S. Appl. No. 11/956,949, filed Dec. 14, 2007, 7 pgs.
Final Office Action dated Jun. 23, 2011; U.S. Appl. No. 11/997,567, filed Mar. 21, 2008, 7 pgs.
Restriction Requirement dated Jun. 29, 2011, U.S. Appl. No. 12/306,945, filed Feb. 9, 2009, 7 pgs.
Werneke et al., Antidepressants and sexual dysfuntion, Acta Psychia. Scand, 2005, 114:384-397.
Response to Final Office Action dated Oct. 12, 2010; U.S. Appl. No. 11/960,957, filed Dec. 20, 2007, 16 pgs.
Interview Summary dated Oct. 19, 2010; U.S. Appl. No. 11/997,567, filed Mar. 21, 2008, 3 pgs.
Response to Final Office Action dated Oct. 21, 2010; U.S. Appl. No. 11/997,567, filed Mar. 21, 2008, 8 pgs.
RCE dated Oct. 21, 2010; U.S. Appl. No. 11/997,567, filed Mar. 21, 2008, 2 pgs.
Interview Substance dated Oct. 21, 2010; U.S. Appl. No. 11/997,567, filed Mar. 21, 2008, 1 pg.
Office Action dated Oct. 26, 2010, U.S. Appl. No. 11/278,551, filed Apr. 4, 2006, 10 pgs.
Office Action dated Nov. 5, 2010; U.S. Appl. No. 11/956,949, filed Dec. 14, 2007, 10 pgs.
Advisory Action dated Nov. 8, 2010; U.S. Appl. No. 11/960,957, filed Dec. 20, 2007, 3 pgs.
Acknowledgment of Priority Document dated Nov. 4, 2010; U.S. Appl. No. 12/091,848, filed Apr. 28, 2008, 1 pg.
Office Action dated Nov. 12, 2010; U.S. Appl. No. 11/997,567, filed Mar. 21, 2008, 7 pgs.
Notice of Allowance dated Nov. 15, 2010; U.S. Appl. No. 12/091,848, filed Apr. 28, 2008, 4 pgs.
RCE dated Dec. 20, 2010; U.S. Appl. No. 12/091,848, filed Apr. 28, 2008, 3 pgs.
Office Action dated Dec. 30, 2010; U.S. Appl. No. 12/390,665, filed Feb. 23, 2009, 9 pgs.
Response to Final Office Action dated Jan. 20, 2011; U.S. Appl. No. 11/745,515, filed May 8, 2007, 7 pgs.
Response to Final Office Action dated Jan. 20, 2011; U.S. Appl. No. 11/554,855, filed Oct. 31, 2006, 9 pgs.
Response to Office Action dated Jan. 28, 2011, U.S. Appl. No. 11/278,551, filed Apr. 4, 2006, 7 pgs.
Response to Final Office Action dated Feb. 7, 2011; U.S. Appl. No. 11/837,957, filed Aug. 13, 2007, 9 pgs.
Final Office Action dated Jul. 9, 2010; U.S. Appl. No. 11/960,957, filed Dec. 20, 2007, 9 pgs.
Response to Final Office Action dated Jul. 20, 2010; U.S. Appl. No. 11/740,959, filed Apr. 27, 2007, 14 pgs.
Response to Office Action dated Jul. 26, 2010; U.S. Appl. No. 11/837,957, filed Aug. 13, 2007, 11 pgs.
Restriction Requirement dated Oct. 4, 2005; U.S. Appl. No. 10/444,892, filed May 22, 2003, 7 pgs.
Response to Restricion Requirement dated Dec. 1, 2003; U.S. Appl. No. 10/444,892, filed May 22, 2003, 2 pgs.
RCE dated Jul. 20, 2010; U.S. Appl. No. 11/740,959, filed Apr. 27, 2007, 3pgs.
Response to Final Office Action dated Aug. 17, 2010; U.S. Appl. No. 11/097,939, filed Apr. 4, 2005, 22 pgs.
RCE dated Aug. 17, 2010; U.S. Appl. No. 11/097,939, filed Apr. 4, 2005, 3 pgs.
RCE dated Sep. 27, 2010, U.S. Appl. No. 11/837,959, filed Aug. 13, 2007, 2 pgs.
Response to Final Office Action dated Sep. 27, 2010, U.S. Appl. No. 11/837,959, filed Aug. 13, 2007, 20 pgs.
Response to Final Office Action dated Sep. 27, 2010 U.S. Appl. No. 11/278,551, filed Apr. 4, 2006, 8 pgs.
Interview Summary dated Jul. 19, 2010; U.S. Appl. No. 11/740,959, filed Apr. 27, 2007, 3 pgs.
Final Office Action dated Aug. 20, 2010 U.S. Appl. No. 11/745,515, filed May 8, 2007, 7 pgs.
Final Office Action dated Aug. 30, 2010 U.S. Appl. No. 11/554,855, filed Oct. 31, 2006, 10 pgs.
Notice of Missing Requirements dated Aug. 24, 2010 U.S. Appl. No. 12/675,231, filed Feb. 25, 2010, 2 pgs.
Interview Summary dated Aug. 25, 2010 U.S. Appl. No. 11/278,551, filed Apr. 4, 2006, 3 pgs.
Final Office Action dated Sep. 13, 2010, U.S. Appl. No. 11/837,962, filed Aug. 13, 2007, 20 pgs.
Office Action dated Sep. 14, 2010; U.S. Appl. No. 11/097,939, filed Apr. 4, 2005, 18 pgs.
Interview Summary dated Sep. 15, 2010, U.S. Appl. No. 11/837,959, filed Aug. 13, 2007, 4 pgs.
Notice of Allowance dated Sep. 20, 2010 U.S. Appl. No. 12/091,848, filed Apr. 28, 2008, 7 pgs.
Final Office Action dated Oct. 6, 2010; U.S. Appl. No. 11/837,957, filed Aug. 13, 2007, 10 pgs.
Richelson, Pharmacology of Antidepressants, Mayo Clin Proc., 2001, 76:511-527.
Freeman et al., Differential Response to Antidepressants in Women With Premenstrual Syndrome/Premenstrual Dysphoric Disorder, Arch Gen Phych, 1999, 56:932-939.
Anonymous: "Hormone Patch May Provide Some Increase in Sexual Desire in Menopausal Women" Jul. 25, 2005: URL:http://pubs.ama-assn.org/media/2005a/0725.dtl , 2 pgs.
FDA (U.S. Food and Drug Adminstration); Reproductive Health Drugs Advisory Committee Meeting Announcement; URL: http://www.fda.gov/AdvisoryCommittees/Calendar/ucm210886.htm; 1 page; Jun. 18, 2010.
Background Document for Meeting of Advisory Committee for Reproductive Health Drugs (Jun. 8, 2010); NDA 22-526 Flibanserin; Boehringer Ingelheim; 80 pp.; May 20, 2010.
Briefing Document; Flibanserin (BIMT 17 BS): Boehringer Ingelheim; 248 pp.; May 14, 2010.
FDA (U.S. Food and Drug Administration); Reproductive Health Drugs Advisory Committee Meeting; Draft Agenda; 1 page; Jun. 18, 2010.
FDA (U.S. Food and Drug Administration); Reproductive Health Drugs Advisory Committee Meeting; Draft Questions to the Committee; 1 page; Jun. 18, 2010.
FDA (U.S. Food and Drug Administration); Reproductive Health Drugs Advisory Committee Meeting; Draft Meeting Roster, 2 pp.; Jun. 18, 2010.
Advisory Committee for Reproductive Health Drugs—2010 Members; 2 pp.; Jun. 2010.
FDA (U.S. Food and Drug Administration); Reproductive Health Drugs Advisory Committee Meeting; Agenda; 2 pp.; Jun. 18, 2010.
FDA (U.S. Food and Drug Administration); Reproductive Health Drugs Advisory Committee Meeting; Questions to the Committee; 1 page; Jun. 18, 2010.

(56) References Cited

OTHER PUBLICATIONS

FDA (U.S. Food and Drug Administration); Reproductive Health Drugs Advisory Committee Meeting; Meeting Roster, 2 pp.; Jun. 18, 2010.
(Slides) Division of Reproductive and Urologic Drug Products Advisory Commitee Meeting: Flibanserin (NDA-22526); Boehringer Ingelheim; 110 pp.; Jun. 18, 2010.
Press Release May 19, 2010; women with hypoactive sexual desire disorder (HSDD) report that fibanserin increased their sexual desire and reduced associated stress; http://www.boehringer-ingelheim.com/news/news releases/press releases/2010/19 May 2010; 4 pp.
Press Release Jun. 17, 2010; Key Facts on HSDD and Flibanserin; http://us.boerhinger-ingelheim.com/news events/press releases/press release archive/2010; 2 pp.
Press Release Jun. 18, 2010; Boehringer Ingelheim comments on Jun. 18 FDA Advisory Committee Meeting; http://us.boehringer-ingelheim.com/news events/press releases; press release archive/2010; 2 pp.
FDA (U.S. Food and Drug Administration); Transcript of Advisory Committee for Reproductive Health Drugs; 293 pgs.; Jun. 18, 2010.
RCE dated May 19, 2010, U.S. Appl. No. 12/170,884, filed Jul. 10, 2008, 3 pgs.
Restriction Requirement dated May 24, 2004 U.S. Appl. No. 10/210,474, filed Aug. 1, 2002 now U.S. Pat. No. 7,183,410, issued Feb. 27, 2007, 6 pgs.
Response to Restriction Requirement dated Jun. 9, 2004 U.S. Appl. No. 10/210,474, filed Aug. 1, 2002 now U.S. Pat. No. 7,183,410, issued Feb. 27, 2007, 2 pgs.
Restriction Requirement dated Aug. 20, 2008, U.S. Appl. No. 11/097,939, filed Apr. 4, 2005, 8 pgs.
Response to Restriction Requirement dated Feb. 12, 2009, U.S. Appl. No. 11/097,939, filed Apr. 4, 2005, 2 pgs.
Restriction Requirement dated Feb. 8, 2007, U.S. Appl. No. 11/110,449, filed Apr. 20, 2005, 8 pgs.
Response to Restriction Requirement dated Jun. 7, 2007, U.S. Appl. No. 11/110,449, filed Apr. 20, 2005, 2 pgs.
Restriction Requirement dated Dec. 23, 2008, U.S. Appl. No. 11/187,422, filed Jul. 22, 2005, 11 pgs.
Restriction Requirement dated May 23, 2007, U.S. Appl. No. 11/364,153, filed Feb. 28, 2006, 7 pgs.
Response to Restriction Requirement dated Sep. 24, 2007, U.S. Appl. No. 11/364,153, filed Feb. 28, 2006, 2 pgs.
Restriction Requirement dated Dec. 18, 2006, U.S. Appl. No. 11/381,590, filed Apr. 4, 2006, 7 pgs.
Response to Restriction Requirement dated Mar. 9, 2007, U.S. Appl. No. 11/381,590, filed Apr. 4, 2006, 2 pgs.
Restriction Requirement dated Aug. 18, 2008; U.S. Appl. No. 11/740,959, filed Apr. 27, 2007, 9 pgs.
Response to Restriction Requirment dated Nov. 18, 2008; U.S. Appl. No. 11/740,959, filed Apr. 27, 2007, 6 pgs.
Restriction Requirement dated Aug. 21, 2009, U.S. Appl. No. 11/837,957, filed Aug. 13, 2007, 7 pgs.
Response to Restriction Requirement dated Sep. 21, 2009, U.S. Appl. No. 11/837,957, filed Aug. 13, 2007, 2 pgs.
Restriction Requirement dated Jun. 21, 2010, U.S. Appl. No. 11/956,949, filed Dec. 14, 2007, 7 pgs.
Restriction Requirement dated Feb. 5, 2009, U.S. Appl. No. 11/960,957, filed Oct. 20, 2007, 8 pgs.
Response to Restriction Requirement dated Mar. 4, 2009, U.S. Appl. No. 11/960,957, filed Oct. 20, 2007, 2 pgs.
Restriction Requirement dated Jun. 30, 2009, U.S. Appl. No. 11/997,567, filed Mar. 21, 2008, 7 pgs.
Response to Restriction Requirement dated Jul. 23, 2009, U.S. Appl. No. 11/997,567, filed Mar. 21, 2008, 2 pgs.
Restriction Requirement dated Oct. 7, 2009, U.S. Appl. No. 12/091,848, filed Apr. 28, 2008, 5 pgs.
Response to Restriction Requirement dated Nov. 9, 2009, U.S. Appl. No. 12/091,848, filed Apr. 28, 2008, 9 pgs.
Restriction Requirement dated May 4, 2010, U.S. Appl. No. 12/279,589, filed Sep. 26, 2008, 9 pgs.
Restriction Requirement dated Sep. 9, 2009, U.S. Appl. No. 11/837,962, filed Aug. 13, 2007, 10 pgs.
Response to Restriction Requirement dated Sep. 25, 2009, U.S. Appl. No. 11/837,962, filed Aug. 13, 2007, 2 pgs.
Notice of Non-Compliant Amendment dated Jun. 22, 2010 U.S. Appl. No. 12/091,848, filed Apr. 28, 2008, 2 pgs.
Response to Notice of Non-Compliant Amendment dated Jun. 23, 2010 U.S. Appl. No. 12/091,848, filed Apr. 28, 2008, 6 pgs.
Response dated Jun. 11, 2010 U.S. Appl. No. 11/837,962, filed Aug. 13, 2007, 16 pgs.
Response dated Jun. 14, 2010 U.S. Appl. No. 12/091,848, filed Apr. 28, 2008, 5 pgs.
U.S. Appl. No. 12/280,804, filed Aug. 27, 2008, Ceci.
U.S. Appl. No. 12/306,946, filed Dec. 29, 2008, Becker.
U.S. Appl. No. 11/956,949, filed Dec. 14, 2007, D'Agostino et al.
U.S. Appl. No. 12/306,878, filed Dec. 29, 2008, Castro et al.
Goldfischer et al., Efficacy of Continued Flibanserin Treatment on Sexual Desire, Satisfying Sexual Events and Sexual Functioning in Premenopausal Women With HSDD: Results From the Researching Outcomes on Sustained Efficacy (ROSE) Study, International Society for the Study of Womens Sexual Health (ISSWSH) annual meeting, 2008, 17 pgs. (oral presentaion).
Final Office Action dated May 21, 2010, U.S. Appl. No. 11/997,567, filed Mar. 21, 2008, 7 pgs.
Final Office Action dated May 27, 2010, U.S. Appl. No. 11/278,551, filed Apr. 4, 2006, 8 pgs.
Examiner's Search Strategy dated May 27, 2010, U.S. Appl. No. 11/278,551, filed Apr. 4, 2006, 3 pgs.
Response dated Jun. 4, 2010, U.S. Appl. No. 11/554,855, filed Oct. 31, 2006, 10 pgs.
Response dated Jun. 4, 2010, U.S. Appl. No. 11/745,515, filed May 8, 2007, 8 pgs.
Advisory Action dated Feb. 10, 2009, U.S. Appl. No. 11/381,130, filed May 2, 2006, 3 pgs.
Final Office Action dated Jul. 18, 2008, U.S. Appl. No. 11/381,130, filed May 2, 2006, 17pgs.
Office Action dated Oct. 9, 2007, U.S. Appl. No. 11/381,130, filed May 2, 2006, 13 pgs.
Response to Final Office Action dated Jan. 21, 2009, U.S. Appl. No. 11/381,130, filed May 2, 2006, 13 pgs.
Response dated Apr. 9, 2008, U.S. Appl. No. 11/381,130, filed May 2, 2006, 36 pgs.
Office Action dated Jun. 1, 2009, U.S. Appl. No. 11/364,306, filed Feb. 28, 2006, 18 pgs.
Examiner's Search Strategy dated Jun. 1, 2009, U.S. Appl. No. 11/364,306, 3 pgs.
Final Office Action dated Sep. 4, 2008, U.S. Appl. No. 11/364,153, filed Feb. 28, 2006, 12 pgs.
Office Action dated Nov. 29, 2007, U.S. Appl. No. 11/364,153, filed Feb. 28, 2006, 11 pgs.
Response dated May 29, 2008, U.S. Appl. No. 11/364,153, filed Feb. 28, 2006, 62 pgs.
Office Action dated Apr. 29, 2009, U.S. Appl. No. 11/364,785, filed Feb. 28, 2006, 23 pgs.
Examiner's Search Strategy dated Apr. 29, 2009, U.S. Appl. No. 11/364,785, filed Feb. 28, 2006, 19 pgs.
Office Action dated Jan. 14, 2010, U.S. Appl. No. 12/091,848, filed Apr. 28, 2008, 5 pgs.
Examiner's Search Strategy dated Jan. 14, 2010, U.S. Appl. No. 12/091,848, filed Apr. 28, 2008, 47 pgs.
Office Action dated Apr. 9, 2009, U.S. Appl. No. 12/170,884, filed Jul. 10, 2008, 10 pgs.
Response dated Oct. 9, 2009, U.S. Appl. No. 12/170,884, filed Jul. 10, 2008, 3 pgs.
Examiner's Search Strategy dated Feb. 19, 2010, U.S. Appl. No. 12/170,884, filed Jul. 10, 2008, 26 pgs.
Examiner's Interview Summary dated Feb. 19, 2010, U.S. Appl. No. 12/170,884, filed Jul. 10, 2008, 4 pgs.
Notice of Allowance dated Feb. 19, 2010, U.S. Appl. No. 12/170,884, filed Jul. 10, 2008, 5 pgs.
Office Action dated Mar. 5, 2009, U.S. Appl. No. 11/740,959, filed Apr. 27, 2007, 30 pgs.

(56) References Cited

OTHER PUBLICATIONS

Response dated Sep. 3, 2009, U.S. Appl. No. 11/740,959, filed Apr. 27, 2007, 12 pgs.
Examiner's Search Strategy dated Mar. 5, 2009, U.S. Appl. No. 11/740,959, filed Apr. 27, 2007, 12 pgs.
Final Office Action dated Jan. 20, 2010; U.S. Appl. No. 11/740,959, filed Apr. 27, 2007, 33 pgs.
Examiner's Search Strategy dated Jan. 20, 2010, U.S. Appl. No. 11/740,959, filed Apr. 27, 2007, 6 pgs.
Office Action dated Apr. 13, 2009, U.S. Appl. No. 11/097,939, filed Apr. 4, 2005, 12 pgs.
Amendment and Response dated Sep. 14, 2009, U.S. Appl. No. 11/097,939, filed Apr. 4, 2005, 8 pgs.
Examiner's Search Strategy dated Apr. 13, 2009, U.S. Appl. No. 11/097,939, filed Apr. 4, 2005, 3 pgs.
Final Office Action dated Feb. 17, 2010, U.S. Appl. No. 11/097,939, filed Apr. 4, 2005, 16 pgs.
Examiner's Search Strategy dated Feb. 17, 2010, U.S. Appl. No. 11/097,939, filed Apr. 4, 2005, 2 pgs.
Office Action dated Mar. 19, 2009, U.S. Appl. No. 11/554,855, filed Oct. 31, 2006, 11 pgs.
Response dated Aug. 19, 2009, U.S. Appl. No. 11/554,855, filed Oct. 31, 2006, 7 pgs.
Examiner's Search Strategy dated Mar. 19, 2009, U.S. Appl. No. 11/554,855, filed Oct. 31, 2006, 3 pgs.
Office Action dated Dec. 4, 2009, U.S. Appl. No. 11/554,855, filed Oct. 31, 2006, 15 pgs.
Examiner's Search Strategy dated Dec. 4, 2009, U.S. Appl. No. 11/554,855, filed Oct. 31, 2006, 3 pgs.
Office Action dated Mar. 19, 2009, U.S. Appl. No. 11/745,515, filed May 8, 2007, 11 pgs.
Office Action dated Dec. 4, 2009, U.S. Appl. No. 11/745,515, filed May 8, 2007, 16 pgs.
Examiner's Search Strategy dated Mar. 19, 2009, U.S. Appl. No. 11/745,515, filed May 8, 2007, 3 pgs.
Response dated Aug. 19, 2009, U.S. Appl. No. 11/745,515, filed May 8, 2007, 8 pgs.
Examiner's Search Strategy dated Dec. 4, 2009, U.S. Appl. No. 11/745,515, filed May 8, 2007, 3 pgs.
Office Action dated Oct. 11, 2005, U.S. Appl. No. 10/882,613, filed Jul. 1, 2004, 7 pgs.
Examiner's Search Strategy dated Oct. 2, 2005, U.S. Appl. No. 10/882,613, filed Jul. 1, 2004, 17 pgs.
Advisory Action dated Mar. 16, 2007, U.S. Appl. No. 10/444,892, filed May 22, 2003, 2 pgs.
Advisory Action dated Mar. 29, 2007, U.S. Appl. No. 10/444,892, filed May 22, 2003, 3 pgs.
Examiner's Interview Summ. dated Oct. 4, 2007, U.S. Appl. No. 10/444,892, filed May 22, 2003, 2 pgs.
Final Office Action dated Aug. 29, 2006, U.S. Appl. No. 10/444,892, filed May 22, 2003, 7 pgs.
Office Action dated Mar. 1, 2006, U.S. Appl. No. 10/444,892, filed May 22, 2003, 5 pgs.
Amendment After Final dated Feb. 28, 2007, U.S. Appl. No. 10/444,892, filed May 22, 2003, 8 pgs.
Amendment dated Jun. 27, 2006, U.S. Appl. No. 10/444,892, filed May 22, 2003, 5 pgs.
Office Action dated Jul. 2, 2007, U.S. Appl. No. 11/110,449, filed Apr. 20, 2005, 11 pgs.
Examiner's Search Strategy dated Jun. 20, 2007, U.S. Appl. No. 11/110,449, filed Apr. 20, 2005, 7 pgs.
Office Action dated Jun. 29, 2009, U.S. Appl. No. 11/960,957, filed Oct. 20, 2007, 12 pgs.
Response dated Dec. 29, 2009, U.S. Appl. No. 11/960,957, filed Oct. 20, 2007, 10 pgs.
Examiner's Search Strategy dated Jun. 29, 2009, U.S. Appl. No. 11/960,957, filed Oct. 20, 2007, 1 pgs.
Notice of Non-Compliant Amendment dated Mar. 10, 2010, U.S. Appl. No. 11/960,957, filed Oct. 20, 2007, 2 pgs.
Amendment and Response to Notice of Non-Compliant Amendment dated Apr. 9, 2010, U.S. Appl. No. 11/960,957, filed Oct. 20, 2007, 5 pgs.
Office Action dated Jan. 26, 2007, U.S. Appl. No. 11/178,716, filed Jul. 11, 2005, 8 pgs.
Office Action dated Apr. 14, 2006, U.S. Appl. No. 11/178,716, filed Jul. 11, 2005, 8 pgs.
Amendment dated Jul. 25, 2006, U.S. Appl. No. 11/178,716, filed Jul. 11, 2005, 5 pgs.
Examiner's Search Strategy dated Jan. 21, 2007, U.S. Appl. No. 11/178,716, filed Jul. 11, 2005, 1 pg.
Examiner's Search Strategy dated Mar. 30, 2006, U.S. Appl. No. 11/178,716, filed Jul. 11, 2005, 15 pgs.
Examiner's Search Strategy dated Apr. 11, 2006, U.S. Appl. No. 11/178,716, filed Jul. 11, 2005, 1 pg.
Final Office Action dated May 18, 2007, U.S. Appl. No. 11/218,107, filed Sep. 1, 2005, 11 pgs.
Office Action dated Aug. 15, 2006, U.S. Appl. No. 11/218,107, filed Sep. 1, 2005, 8 pgs.
Response dated Feb. 14, 2007, U.S. Appl. No. 11/218,107, filed Sep. 1, 2005, 4 pgs.
Examiner's Search Strategy dated Jun. 30, 2006, U.S. Appl. No. 11/218,107, filed Sep. 1, 2005, 8 pgs.
Examiner's Search Strategy dated Aug. 11, 2006, U.S. Appl. No. 11/218,107, filed Sep. 1, 2005, 2 pgs.
Office Action dated Aug. 26, 2008, U.S. Appl. No. 11/940,655, filed Nov. 15, 2007, 7 pgs.
Office Action dated Sep. 28, 2009, U.S. Appl. No. 11/997,567, filed Mar. 21, 2008, 7 pgs.
Examiner's Search Strategy dated Sep. 28, 2009, U.S. Appl. No. 11/997,567, filed Mar. 21, 2008, 43 pgs.
Response dated Feb. 19, 2010, U.S. Appl. No. 11/997,567, filed Mar. 21, 2008, 10 pgs.
Office Action dated Jan. 25, 2010, U.S. Appl. No. 11/837,957, filed Aug. 13, 2007, 11 pgs.
Examiner's Search Strategy dated Jan. 25, 2010, U.S. Appl. No. 11/837,957, 6 pgs.
Examiner's Interview Summ. dated Oct. 2, 2009, U.S. Appl. No. 11/837,959, filed Aug. 13, 2007, 2 pgs.
Office Action dated Jul. 20, 2009, U.S. Appl. No. 11/837,959, filed Aug. 13, 2007, 8 pgs.
Examiner's Search Strategy dated Jul. 20, 2009, U.S. Appl. No. 11/837,959, filed Aug. 13, 2007, 5 pgs.
Final Office Action dated Mar. 25, 2010, U.S. Appl. No. 11/837,959, filed Aug. 13, 2007, 12 pgs.
Response dated Jan. 20, 2010, U.S. Appl. No. 11/837,959, filed Aug. 13, 2007, 11 pgs.
Office Action dated Jan. 11, 2010, U.S. Appl. No. 11/837,962, filed Aug. 13, 2007, 17 pgs.
Examiner's Search Strategy dated Jan. 11, 2010, U.S. Appl. No. 11/837,962, filed Aug. 13, 2007, 8 pgs.
Ferger et al., Flibranserin, a drug intended for treatment of hypoactive sexual desire disorder in pre-menopausal women, affects spontaneous motor activity and brain neurochemistry in female rates, Naunyn Schmiedebergs Arch Pharmacol., Apr. 27, 2010, pp. 1-17 (epub ahead of print).
Aubert et al., Comparison of Flibanserin With the 5-Htla Agonist (+)-8-Oh-Dpat in Affecting Interactions Between Male-Female Marmoset Pairs, J. Sex Med., May 2010, 7(s3):118. (abstract).
Aubert et al., Initial PET Assessment of Flibanserin-induced Neural Changes in Female Marmoset Monkeys, J. Sex Med., May 2010, 7(s3):131. (abstract).
Aubert et al., Chronic Treatment of Female Marmoset Monkeys with (+)-8-OH-DPAT or Flibanserin Differentially Alters Response of the Hypothalamic-Pituitary-Adrenal Axis to Restraint and Acute Serotonergic Challenge, J. Sex Med., May 2010, 7(s3):131. (abstract).
Gelez et al., Chronic Flibanserin Treatment Increases Solicitations in the Female Rat, J. Sex Med., May 2010, 7(s3):118. (abstract).
Allers et al., Acute and Repeated Flibanserin Administration in Female Rats Modulates Monoamines Differentially Across Brain Areas: A Microdialysis Study, J. Sex Med., Feb. 2010, 33 pgs. (Epub ahead of print).

(56) References Cited

OTHER PUBLICATIONS

Dennerstein et al., Differentiating Four Cognitive-Behavioral Types of Women with Decreased Sexual Desire, International Society for the Study of Womens Sexual Health (ISSWSIT) annual meeting, 2007, 2 pgs. (abstract).
Dennerstein et al., Differentiating Four Cognitive-Behavioral Types of Women with Decreased Sexual Desire, American Psychiatric Association (APA) annual meeting, 2007, 3 pgs. (poster and abstract).
Dennerstein et al., Differentiating Four Cognitive-Behavioral Types of Women with Decreased Sexual Desire, European Society for Sexual Medicine (ESSM) annual meeting, 2007, 3 pgs. (poster and abstract).
Dennerstein, Differentiating Four Cognitive-Behavioral Types of Women with Low Sexual Desire, European Society for Sexual Medicine (ESSM) annual meeting, 2007, 10 pgs. (oral presentation).
Dennerstein et al., Attitudes Towards Partner Interactions of Women With Characteristics of HSDD: Preliminary Results of a Multinational Study of 1,402 Women. International Society for the Study of Womens Sexual Health (ISSWSH) annual meeting, 2008, 12 pgs. (oral presentation and abstract).
Goldfischer et al., Validation of the Decreased Sexual Desire Screener (DSDS): a Brief Diagnostic Instrument for Generalized, Acquired Hypoactive Sexual Desire Disorder in Women, American Psychiatric Association (APA) annual meeting, 2007, 2 pgs. (poster and abstract).
Pyke et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (poster).
Goldfischer et al., Efficacy of Continued Flibanserin Treatment on Sexual Desire and Satisfying Sexual Events in Premenopausal Women with HSDD: Results From the ROSE Study, International Society for the Study of Womens Sexual Health (ISSWSH) annual meeting, 2008, 1 pgs. (abstract).
Goldfischer et al., Efficacy of Continued Flibanserin Treatment of Distress Associated with Sexual Dysfunction in Premenopausal Women With HSDD: Results From the ROSE Study, International Society for the Study of Womens Sexual Health (ISSWSH) annual meeting, 2008, 2 pgs. (poster and abstract).
Goldfischer et al., Efficacy of Continued Flibanserin Treatment on Sexual Functioning in Premenopausal Women With HSDD: Results From the ROSE Study, International Society for the Study of Womens Sexual Health (ISSWSH) annual meeting, 2008, oral presentation, 1 pg. (abstract only).
Goldfischer et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOO) annual meeting, 2008, 1 pgs. (abstract only).
Goldfischer et al., The ROSE Study: Placebo-controlled Randomized Withdrawal Trial of Flibanserin for Hypoactive Sexual Desire Disorder in Premenopausal Women, European Federation of Sexology (EFS), 2008, 7 pgs. (oral presentation and abstract).
Goldfischer et al., Decreased Sexual Desire Screener (DSDS) for Diagnosis of Hypoactive Sexual Desire Disorder in Women, American College of Obstetrics and Gynecologists (ACOG) annual meeting, 2008, 2 pgs. (poster and abstract).
Goldfischer et al., Efficacy of Continued Flibanserin Treatment in Premenopausal Women with Hypoactive Sexual Desire Disorder: Results from the ROSE Study, International Academy of Sex Research (IASR) annual meeting, 2008, 3 pgs. (poster and abstract).
Goldfischer et al., Safety and Tolerability of Flibanserin in Premenopausal Women with Hypoactive Sexual Desire Disorder: Results from the ROSE Study, International Academy of Sex Research (IASR) annual meeting, 2008, 3 pgs. (poster and abstract).
Goldfischer et al., Efficacy and Safety of Flibranserin in Premenopausal Women with Hypoactive Sexual Desire Disorder: Results from the Randomized Withdrawal ROSE Study, Institute on Psychiatric Services (IPS) annual meeting, 2008, 2 pgs. (poster and abstract).
Goldfischer et al., Decreased Sexual Desire Screener (DSDS) for Diagnosis of Hypoactive Sexual Desire Disorder in Women, Sexual Medicine Society of North America (SMSNA) annual meeting, 2008, 3 pgs. (poster and abstract).
Goldfischer et al., Efficacy and Safety of Flibanserin in Premenopausal Women with Hypoactive Sexual Desire Disorder: Results From the Randomized Withdrawal ROSE Study, Sexual Medicine Society of North America (SMSNA) annual meeting, 2008, 3 pgs. (poster and abstract).
Goldfischer, Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 10 pgs. (oral presentation).
Goldfischer et al., Efficacy of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (abstract).
Golffischer et al., Safety and Tolerability of Continued Flibanserin Treatment in Premenopausal Women with Hypoactive Sexual Desire Disorder: Results From the ROSE Study, Joint Congress of the European and International Societies of Sexual Medicine (ESSM/ISSM), 2008, 2 pgs. (poster and abstract).
Goldstein et al., Differences in Patient-Physician Communication Regarding Hypoactive Sexual Desire Disorder (HSDD), Sexual Medicine Society of North America (SMSNA) annual meeting, 2007, 3 pgs. (poster and abstract).
Goldstein et al., Emotions Related to Distress in Patients with Hypoactive Sexual Desire Disorder: Results of Patient and Physician Interviews, Sexual Medicine Society of North America (SMSNA) annual meeting, 2007, 3 pgs. (poster and abstract).
Jolly et al., Design of Phase III Pivotal Trials of Flibanserin in Female Hypoactive Sexual Desire Disorder (HSDD), European Federation of Sexology (EFS), 2008, 2 pgs. (poster and abstract).
Konarski et al., Effects of Acute Flibanserin on FDG-PET Brain Glucose Metabolism in Men with Major Depressive Disorder, European College of Neuropsychopharmacology congress (ECNP), 2008, 3 pgs. (poster and abstract).
Nappi et al., Validation of the Sexual Interest and Desire Inventory-Female (SIDI-F) in European Women, European Federation of Sexology (EFS), 2008, 2 pgs. (poster and abstract).
Nappi, Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 8 pgs. (oral presentation).
Nappi et al., Decreased Sexual Desire Screener (DSDS) for Diagnosis of Hypoactive Sexual Desire Disorder (HSDD) in European Women, Joint Congress of the European and International Societies of Sexual Medicine (ESSM/ISSM), 2008, 1 pg. (abstract).
Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 8 pgs. (oral presentation).
Nappi et al., Decreased Sexual Desire Screener (DSDS) for Diagnosis of Hypoactive Sexual Desire Disorder (HSDD) in European Women, International Society for the Study of Womens Sexual Health (ISSWSH) annual meeting, 2009, oral presentation, 1 pg. (abstract).
Pyke et al., Using e-Diaries to Measure Sexual Desire in Women with Hypoactive Sexual Desire Disorder, American Psychiatric Association (APA) annual meeting, 2007, 2 pgs. (poster and abstract).
Pyke et al., The ROSE Study: Placebo-Controlled Randomized Withdrawal Trial of Flibanserin for Hypoactive Sexual Desire Disorder in Premenopausal Women (Study Design Only), Institute on Psychiatric Services (IPS) annual meeting, 2007, 2 pgs. (poster and abstract).
Pyke et al., Safety and Tolerability of Flibanserin in Premenopausal Women With Hypoactive Sexual Desire Disorder (HSDD): Results

(56) References Cited

OTHER PUBLICATIONS

From the ROSE Study, American Psychiatric Association (APA) annual meeting, 2008, 2 pgs. (poster and abstract).
Pyke et al., Flibanserin: a Novel Centrally Acting Agent That is not an Effective Antidepressant but has Potential to Treat Decreased Sexual Desire in Women, American Psychiatric Association (APA) annual meeting, 2008, 2 pgs. (poster and abstract).
Rosen et al., The Predictors of Sexual Distress in Women With Low Sexual Desire, International Society for the Study of Womens Sexual Health (ISSWSH) annual meeting, 2009, oral presentation, 15 pgs. (oral presentation and abstract).
Shifren et al., Sexual Problems and Distress in United States Women: Prevalence and Correlates , Obstet. Gynecology, Nov. 2008, 112(5):970-978.
Shifren et al., Treatment-seeking Behavior of U.S. Women with Hypoactive Sexual Desire Disorder (HSDD), American College of Obstetrics and Gynecologists (ACOG) annual meeting, 2008, 2 pgs. (poster and abstract).
Pyke et al., Validation of the Sexual Interest and Desire Inventory-Female (SIDI-F) in European Women, International Society for the Study of Womens Sexual Health (ISSWSH) annual meeting, 2007, 20 pgs. (oral presentation).
Nappi et al., Validation of the Sexual Interest and Desire Inventory-Female (SIDI-F) in European Women, European Society for Sexual Medicine (ESSM) annual meeting, 2007, 19 pgs. (oral presentation).
Sand et al., The Female Sexual Function Index (FSFI): A Potential "Gold Standard" Measure for Assessing Therapeutically-Induced Change in Female Sexual Function, ASRM, 2009, Oct. 17-21, 2009, Atlanta, Georgia, 2 pgs. (poster and abstract).
Smith et al., Pharmacokinetics of Flibanserin in Premenopausal Women With Hypoactive Sexual Desire Disorder Including Effects on the Female Sexual Function Index, ESSM, 2009, Nov. 2009, 2 pgs., Lyon. (poster and abstract).
Clayton et al., Efficacy of Flibanserin as a Potential Treatment for Hypoactive Sexual Desire Disorder in North American Premenopausal Women: Results From the Dahlia Trial, ESSM, 2009, Nov. 2009, 2 pgs., Lyon. (poster and abstract).
Thorp et al., Efficacy of Flibanserin as a Potential Treatment for Hypoactive Sexual Desire Disorder in North American Premenopausal Women: Results From the Daisy Trial, ESSM, 2009, Nov. 2009, 3 pgs., Lyon. (poster and abstract).
Jolly et al., Design of Randomized Controlled Trials of Flibanserin in Premenopausal Women With Hypoactive Sexual Desire Disorder, ESSM 2009, Nov. 2009, 3 pgs., Lyon. (poster and abstract).
Revicki et al., Content Validity of the Female Sexual Function Index in Pre- and Postmenopausal Women With Hypoactive Sexual Desire Disorder, ESSM 2009, Nov. 2009, 2 pgs., Lyon. (poster and abstract).
Aubert et al., Comparison of Flibanserin With the 5-Htla Agonist (+)-8-Oh-Dpat in Affecting Interactions Between Male-Female Marmoset Pairs, ESSM 2009, Nov. 2009, 2 pgs., Lyon (poster and abstract).
Rosen et al., Criterion Validity of the Sexual Desire Domain of the Female Sexual Function Index (Fsfi): Identifying a Diagnostic Cut-Point for Differentiating Women With and Without Hsdd, ESSM 2009, Nov. 2009, 3 pgs., Lyon. (poster and abstract).
Rosen et al., Validation of the FSFI Sexual Desire Domain Diagnostic Cut-Point in Predicting Hsdd in Women: Independent Replication and Confirmation, ESSM 2009, Nov. 2009, 2 pgs., Lyon. (poster and abstract).
Nappi, Efficacy of Flibanserin as a Potential Treatment for Hypoactive Sexual Desire Disorder in European Premenopausal Women: Results From the Orchid Trial: ESSM 2009, Nov. 2009, 12 pgs., Lyon. (oral presentation).
Nappi et al., Efficacy of Flibanserin as a Potential Treatment for Hypoactive Sexual Desire Disorder in European Premenopausal Women: Results From the Orchid Trial; ESSM 2009, Nov. 2009, 1 pg., Lyon. (abstract).

Holstege et al., Differences in Brain Activity in Premenopausal Women With Hypoactive Sexual Desire Disorder (Hsdd) Compared to Women Without Sexual Dysfunction, ESSM 2009, Nov. 2009, 2 pgs., Lyon. (abstract only).
Holstege et al., Brain activation and de-activation caused by erotic movies is lower in HSDD- than in non-HSDD volunteers, ESSM 2009, 8 pgs. (oral presentaion).
Jolly, Efficacy of Flibanserin 100 Mg Qhs as a Potential Treatment for Hypoactive Sexual Desire Disorder in Premenopausal Women, ESSM 2009, Nov. 2009, 12 pgs., Lyon. (oral presentation).
Jolly et al., Efficacy of Flibanserin 100 Mg Qhs as a Potential Treatment for Hypoactive Sexual Desire Disorder in Premenopausal Women, ESSM 2009, Nov. 2009, 1 pgs., Lyon. (abstract).
Jolly et al., Efficacy of Flibanserin 100 Mg Qhs as a Potential Treatment for Hypoactive Sexual Desire Disorder in North American Premenopausal Women, ESSM 2009, Nov. 2009, 2 pgs., Lyon. (poster and abstract).
Clayton, Safety and Tolerability of Flibanserin in Premenopausal Women With Hypoactive Sexual Desire Disorder, ESSM 2009, Nov. 2009, 12 pgs., Lyon. (oral presentation).
Jolly et al., Safety and Tolerability of Flibanserin in Premenopausal Women With Hypoactive Sexual Desire Disorder, ESSM 2009, Nov. 2009, 1 pgs., Lyon. (abstract).
Jolly et al., Efficacy of Flibanserin as a Potential Treatment for Hypoactive Sexual Desire Disorder in North American Premenopausal Women: Results From the Violet Trial, ESSM 2009, Nov. 2009, 3 pgs., Lyon. (poster and abstract).
Fuchs, Baseline Characteristics of Patients Enrolled in Three Phase III North Ameican Trials of Flibanserin in Premenopausal Women With Hypoactive Sexual Desire Disorder, FIGO 2009, Oct. 2009, 10 pgs., Cape Town, South Africa. (oral presentation).
Goldfischer, Efficacy and Safety of Flibanserin in a Randomized Withdrawal Study of Premenopausal Women With Hypoactive Sexual Desire Disorder, FIGO2009, Oct. 2009, 12 pgs., Cape Town, South Africa. (oral presentation).
Goldfischer et al., Efficacy and Safety of Flibanserin in a Randomized Withdrawal Study of Premenopausal Women With Hypoactive Sexual Desire Disorder, FIGO2009, Oct. 2009, 1 pgs., Cape Town, South Africa. (abstract).
Revicki et al., Content Validity of the Female Sexual Function Index in Pre- and Postmenopausal Women With Hypoactive Sexual Desire Disorder, ICSM 2009, Jul. 2009, 2 pgs., Paris. (poster and abstract).
Revicki et al., Content Validity of the Female Sexual Function Index in Pre-Menopausal Women With Hypoactive Sexual Desire Disorder, ICSM 2009, Jul. 2009, 2 pgs., Paris. (poster and abstract).
Rosen et al., Criterion Validity of the Sexual Desire Domain of the Female Sexual Funcion Index (Fsfi): Identifying a Diagnostic Cut-Point for Differentiating Women With and Without Hsdd, ICSM 2009, Jul. 2009, 2 pgs., Paris. (poster and abstract).
Rosen et al., Validation of the Fsfi Sexual Desire Domain Diagnostic Cut-Point in Predicting Hsdd: Independent Replication and Confirmation, ICSM 2009, Jul. 2009, 2 pgs., Paris. (poster and abstract).
Sand et al., The Female Sexual Function Index (Fsfi): A Potential "Gold Standard" Measure for Assessing Sexual Function in Women, ICSM 2009, Jul. 2009, 2 pgs., Paris. (poster and abstract).
Jayne, Results From the Dahlia (511.70) Trial: A Prospective Study of Flibanserin for the Treatment of Hypoactive Sexual Desire Disorder in North American Premenopausal Women, SMSNA 2009, Nov. 2009, 3 pgs., San Diego, USA (oral presentation).
Jayne et al., Results From the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).
Sand et al., Efficacy of Flibanserin in North American Premenopausal Women With Hypoactive Sexual Desire Disorder: Results From the Daisy Trial, SMSNA 2009, Nov. 2009, 2 pgs., San Diego, USA. (poster and abstract).
Sand, Efficacy of Flibanserin in North American Premenopausal Women With Hypoactive Sexual Desire Disorder: Results From the Daisy Trial, SMSNA 2009, Nov. 2009, 2 pgs., San Diego, USA. (oral presentation).
Sand et al., The Female Function Index (Fsfi) is a Potential "Gold Standard" Measure for Assessing Sexual Function in Pre- and

(56) References Cited

OTHER PUBLICATIONS

Post-Menopausal Women: A Systematic Review, SMSNA 2009, Nov. 2009, 2 pgs., San Diego, USA. (poster and abstract).
Sand et al., Efficacy of Flibanserin 100 Mg Qhs as a Potential Treatment for Hypoactive Sexual Desire Disorder in North American Premenopausal Women, SMSNA 2009, Nov. 2009, 2 pgs., San Diego, USA. (poster and abstract).
Sand, Efficacy of Flibanserin 100 Mg Qhs as a Portential Treatment for Hypoactive Sexual Desire Disorder in North American Premenopausal Women, SMSNA 2009, Nov. 2009, 2 pgs., San Diego, USA. (oral presentation).
Holstege et al., Difference in Brain Activity in Premenopausal Women With Hypoactive Sexual Desire Disorder (Hsdd) Compared to Women Without Sexual Dysfunction, SMSNA 2009, Nov. 2009, 2 pgs., San Diego, USA (abstract only).
Holstege et al., Brain activation and de-activation caused by erotic movies in lower in HSDD- than in non-HSDD volunteers, SMSNA, 2009, 4 pgs (poster & oral presentation).
Sand et al., Pooled Clinical Trial Analysis of Flibanserin Safety and Tolerability in Premenopausal Women with Hypoactive Sexual Desire Disorder, SMSNA, 2009, 2 pgs. (poster and abstract).
Sand, Pooled Clinical Trial Analysis of Flibanserin Safety and Tolerability in Premenopausal Women with Hypoactive Sexual Desire Disorder, SMSNA, 2009, 2 pgs. (oral presentation).
Sand et al., Effacacy of Flibanserin in North American Premenopausal Women with Hypoactive Sexual Desire Disorder: Results from the Violet Trial, SMSNA, 2009, 3 pgs. (poster and abstract).
Sand, Effacacy of Flibanserin in North American Premenopausal Women with Hypoactive Sexual Desire Disorder: Results from the Violet Trial, SMSNA, 2009, 2 pgs. (oral presentation).
Meston, The Female Sexual Function Index (FSFI) is a Potential "Gold Standard" Measure for Assessing Sexual Function in Pre- and post-menopausal Women: a Systematic Review, SMSNA, 2009, 3 pgs. (oral presentation).
Goldfischer, Efficacy and Safety of Flibanerin in a Randomized Withdrawal Study of Premenopausal Women With Hypoactive Sexual Desire Disorder, WAS, 2009, 12 pgs. (oral presentation).
Goldfischer et al., Efficacy and Safety of Flibanserin in a Randomized Withdrawal Study of Premenopausal Women With Hypoactive Sexual Desire Disorder, WAS, 2009, 1 pgs. (abstract).
Clayton et al., Baselin Characteristics of Patients Enrolled in Three Phase III North American Trials of Flibanserin in Premenopausal Women with Hypoactive Sexual Desire Disorder, WAS, 2009, 2 pgs. (poster and abstract).
Clayton, Baseline Characteristics of Patients Enrolled in Three Phase III North American Trials of Flibanserin in Premenopausal Women with Hypoactive Sexual Desire Disorder, WAS, 2009, 4 pgs. (oral presentation).
Derogatis et al., Content Validity of the Female Sexual Distress Scale-Revised in Women With Hypoactive Sexual Desire Disorder, WAS, 2009, 1 pg. (abstract only).
Dennerstein et al., Attitudes Toward and Frequency of Partner Interactions Among Women Reporting Decreased Sexual Desire, J. Sex Med., 2009, 6:1668-1673.
Goldstein et al., National Differences in Patient-Clinician Communication Regarding Hypoactive Sexual Desire Disorder, J. Sex Med., 2009, 6:1349-1357.
Johannes et al., Distressing Sexual Problems in United States Women Revisited: Prevalence After Accounting for Depression, J. Clin. Psych., 2009, 70(12):1698-1706.
Pfaus, Pathways of Sexual Desire, J. Sex Med., 2009, 6:1506-1533.
Rosen et al., Correlates of Sexually Related Personal Distress in Women with Low Sexual Desire, J. Sex Med., 2009, 6:1549-1560.
Shifren et al., Help-Seeking Behavior of Women with Self-Reported Distressing Sexual Problems, J. of Women's Health, 2009, 18(4):461-468.
Wunderlich et al., Validity of Sexual Distress Scales vs Electronic Diary in Women with Decreased Sexual Desire, American College of Obstetrics and Gynecologists (ACOG) annual meeting, 2007, 1 pg. (poster).
Lewis-D' Agostino et al., Validating the Sexual Interest and Desire Inventory (SIDI-F) in North American Women, American College of Obstetrics and Gynecologists (ACOG) annual meeting, 2007, 1 pg. (poster).
Clayton et al., Using e-Diaries to Measure Sexual Desire in Women with Hypoactive Sexual Desire Disorder, European Society for Sexual Medicine (ESSM) annual meeting, 2007, 2 pgs. (abstract).
Van Lunsen et al., Validation of the Sexual Interest and Desire Inventory-Female (SIDI-F) in European Women, European Society for Sexual Medicine (ESSM) annual meeting, 2007, 1 pg. (abstract).
Clayton et al., Using e-Diaries to Measure Sexual Desire in Women with Hypoactive Sexual Desire Disorder, International Society for the Study of Womens Sexual Health (ISSWSH) annual meeting, 2007, 2 pgs. (abstract).
Van Lundsen, Validation of the Sexual Interest and Desire Inventory-Female (SIDI-F) in European women, ISSWSH, 2007, 2 pgs. (abstract).
Goldfischer et al., The ROSE Study: Placebo-controlled Randomized Withdrawal Trial of Flibanserin for Hypoactive Sexual Desire Disorder in Premenopausal Women, Sexual Medicine Society of North America (SMSNA) annual meeting, 2007, 1 pg. (abstract).
Krychman et al., The ROSE Study: Placebo-controlled Randomized Withdrawal Trial of Flibanserin for Hypoactive Sexual Desire Disorder in Premenopausal Women, European Board and College of Obstetrics and Gynaecology (EBCOG) annual meeting, 2008, 6 pgs. (poster and oral presentation).
Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pgs., Cape Town, South Africa. (abstract).
Scandroglio et al., Ex Vivo binding of Flibanserin to Serotonin-5-HT1A and 5-HT2A Receptors, Pharm. Res., 2001, 43(2):179-183.
D'Aquila et al., Anti-anhedonic actions of the novel serotonergic agent flibanserin, a potential rapidly-acting antidepressant, Euro. J. Pharm., 1997, 340:121-132.
Flik et al., Assessment of serotonin and catecholamine levels in the female rat brain following acute and chronic administration with flibanserin, a potential novel treatment for hypoactive sexual desire disorder: An in vivo microdialysis study, presented at Neuroscience 2009, Feb. 3, 2010, http://www.abstractsonline.com/Plan/AbstractPrintView.aspx?mID=2285&sKey=65206 . . . , 2 pgs.
Banfi et al., Benzimidazolone Derivatives: a new class of potative antidepressant agents, 13th Int. Symp. on Medicinal Chemistry, Sep. 19-23, 1994, p. 102. (abstract).
Borsini et la., BIMT 17, a 5-HT1A receptor agonist/5-HT2A receptor antagonist, directly activates portsynaptic 5-HT inhibitory responses in the rat cerebral cortex, Naunyn-Schmiedeberg's Arch Pharm., 1995, 352:283-290.
Boehringer Ingelheim, Flibanserin BIMT-17, Drugs of the Future, 1999, 24(1):91.
Podhorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. for Biomed. and Drug Res., Abstract-Book, Milan, Sep. 6-7, 2000, 1 pg.
Vaccarino et al., Flibanserin, a 5-HT1A agonist/5-HT2A antagonist, decreases sucrose intake in operant and non-operant paradigms in rats, Soc. Neurosci. Abstr., 2000, 26:394:Abstr 144.9, 30th Ann. Mtg. of Soc. for Neurosci, New Orleans, Nov. 4-9, 1000, 1 pg.
Borsini et al., Further characterisation of potential antidepressant action of flibanserin, Psychopharm., 2001, 159:64-69.
Rueter et al., In Vivo Electrophysiological Assessment of the Agonistic Properties of Flibanserin at Pre- and Postsynaptic 5-HT1A Receptors in the Rat Brain, Synapse, 1998, 29:392-405.
Cervo et al., Involvement of 5-HT1A receptors in flibanserin discriminative stimulus in female rats, Neurosci 2009, Feb. 3, 2010, http://www.abstractsonline.com/Plan/AbstratPrintView.aspx?mID=2285&sKey=65206 . . . , 2pgs.
Cervo et al., Involvement of 5-HT1A receptors in flibanserin discriminative stimulus in female rats, Dept. CNS Diseases, Prog. No. 465.20, 2009 Neurosci., Oct. 19, 2009, 1 pg. (poster).
Ferger et al., Neurochemical characterization of Flibanserin a phase III drug for treatment of hypoactive sexual desire disorder (HSDD)

(56) References Cited

OTHER PUBLICATIONS in women, Neurosci 2009, Feb. 3, 2010, http://www.abstractsonline.com/Plan/AbstractPrintView.aspx?mIK=2285&sKey=65206 . . . , 2 pgs.
Flik et al., Assessment of serotonin and catecholamine levels in the female rat brain following acute and chronic administration with flibanserin, a potential novel treatment for hypoactive sexual desire disorder: An in vivo microdialysis study, SFN, 2009, 1 pg. (poster).
Ferger et al., Neurochemical characterization of Flibanserin a phase III drug for treatment of hypoactive sexual desire disorder (HSDD) in women, SFN, 2009, 1 pg. (poster).
Evans et al., The Effects of Flibanserin on Amphetamine Withdrawal-Induced hypolocomotion in Rats, Soc. Neurosci. Abstr., Nov. 7-12, 1998, 24:2133:Abstr 848.5, 28th Ann. Mtg. of the Soc. for Neurosci, Los Angeles, 1 pg.
Advisory Action dated Dec. 27, 2005, U.S. Appl. No. 10/272,603, filed Oct. 16, 2002 now U.S. Pat. No. 7,151,103, issued Dec. 19, 2006, 3 pgs.
Examiner's Interview dated Jun. 23, 2006, U.S. Appl. No. 10/272,603, filed Oct. 16, 2002 now U.S. Pat. No. 7,151,103, issued Dec. 19, 2006, 2 pgs.
Examiner's Interview dated Oct. 20, 2005, U.S. Appl. No. 10/272,603, filed Oct. 16, 2002 now U.S. Pat. No. 7,151,103, issued Dec. 19, 2006, 1 pg.
Final Office Action dated Jun. 2, 2005, U.S. Appl. No. 10/272,603, filed Oct. 16, 2002 now U.S. Pat. No. 7,151,103, issued Dec. 19, 2006, 9 pgs.
Notice of Allowance dated Jun. 23, 2006, U.S. Appl. No. 10/272,603, filed Oct. 16, 2002 now U.S. Pat. No. 7,151,103, issued Dec. 19, 2006, 7 pgs.
Notice of Appeal/Amendment dated Nov. 8, 2005, U.S. Appl. No. 10/272,603, filed Oct. 16, 2002 now U.S. Pat. No. 7,151,103, issued Dec. 19, 2006, 9 pgs.
Office Action dated Oct. 14, 2004, U.S. Appl. No. 10/272,603, filed Oct. 16, 2002 now U.S. Pat. No. 7,151,103, issued Dec. 19, 2006, 8 pgs.
RCE/Supp. Amendment dated Jun. 8, 2006, U.S. Appl. No. 10/272,603, filed Oct. 16, 2002 now U.S. Pat. No. 7,151,103, issued Dec. 19, 2006, 29 pgs.
Reply dated Feb. 14, 2005, U.S. Appl. No. 10/272,603, filed Oct. 16, 2002 now U.S. Pat. No. 7,151,103, issued Dec. 19, 2006, 20 pgs.
Examiner's Search Strategy dated Jun. 20, 2006, U.S. Appl. No. 10/272,603, filed Oct. 16, 2002 now U.S. Pat. No. 7,151,103, issued Dec. 19, 2006, 2 pgs.
Examiner's Search Strategy dated Jun. 21, 2006, U.S. Appl. No. 10/272,603, filed Oct. 16, 2002 now U.S. Pat. No. 7,151,103, issued Dec. 19, 2006, 20 pgs.
Examiner's Search Strategy dated Sep. 22, 2004, U.S. Appl. No. 10/272,603, filed Oct. 16, 2002 now U.S. Pat. No. 7,151,103, issued Dec. 19, 2006, 83 pgs.
Examiner's Search Strategy dated Sep. 28, 2004, U.S. Appl. No. 10/272,603, filed Oct. 16, 2002 now U.S. Pat. No. 7,151,103, issued Dec. 19, 2006, 117 pgs.
Examiner's Search Strategy dated Sep. 29, 2004, U.S. Appl. No. 10/272,603, filed Oct. 16, 2002 now U.S. Pat. No. 7,151,103, issued Dec. 19, 2006, 1 pg.
Examiner's Search Strategy dated Oct. 14, 2004, U.S. Appl. No. 10/272,603, filed Oct. 16, 2002 now U.S. Pat. No. 7,151,103, issued Dec. 19, 2006, 3pgs.
Final Office Action dated Oct. 5, 2005, U.S. Appl. No. 10/210,474, filed Aug. 1, 2002 now U.S. Pat. No. 7,183,410, issued Feb. 27, 2007, 6 pgs.
Notice of Allowance dated Jan. 30, 2006, U.S. Appl. No. 10/210,474, filed Aug. 1, 2002 now U.S. Pat. No. 7,183,410, issued Feb. 27, 2007, 7 pgs.
Notice of Allowance dated Jul. 12, 2006, U.S. Appl. No. 10/210,474, filed Aug. 1, 2002 now U.S. Pat. No. 7,183,410, issued Feb. 27, 2007, 7 pgs.
Office Action dated Mar. 16, 2005, U.S. Appl. No. 10/210,474, filed Aug. 1, 2002 now U.S. Pat. No. 7,183,410, issued Feb. 27, 2007, 9 pgs.
Office Action dated Jul. 26, 2004, U.S. Appl. No. 10/210,474, filed Aug. 1, 2002 now U.S. Pat. No. 7,183,410, issued Feb. 27, 2007, 7 pgs.
Response to Final Office Action dated Dec. 15, 2005, U.S. Appl. No. 10/210,474, filed Aug. 1, 2002 now U.S. Pat. No. 7,183,410, issued Feb. 27, 2007, 9 pgs.
Reply dated Jan. 26, 2005, U.S. Appl. No. 10/210,474, filed Aug. 1, 2002 now U.S. Pat. No. 7,183,410, issued Feb. 27, 2007, 24 pgs.
Amendment dated Jul. 11, 2005, U.S. Appl. No. 10/210,474, filed Aug. 1, 2002 now U.S. Pat. No. 7,183,410, issued Feb. 27, 2007, 13 pgs.
Examiner's Search Strategy dated Mar. 10, 2005, U.S. Appl. No. 10/210,474, filed Aug. 1, 2002 now U.S. Pat. No. 7,183,410, issued Feb. 27, 2007, 36 pgs.
Examiner's Search Strategy dated Sep. 30, 2005, U.S. Appl. No. 10/210,474, filed Aug. 1, 2002 now U.S. Pat. No. 7,183,410, issued Feb. 27, 2007, 6 pgs.
Reply with Amendment dated Mar. 8, 2005, U.S. Appl. No. 10/210,474, filed Aug. 1, 2002 now U.S. Pat. No. 7,183,410, issued Feb. 27, 2007, 10 pgs.
Supplemental Amendment dated Jan. 19, 2006, U.S. Appl. No. 10/210,474, filed Aug. 1, 2002 now U.S. Pat. No. 7,183,410, issued Feb. 27, 2007, 6 pgs.
Examiner's Interview dated Nov. 19, 2007, U.S. Appl. No. 11/546,303, filed Oct. 12, 2006, 3 pgs.
Final Office Action dated Sep. 14, 2007, U.S. Appl. No. 11/546,303, filed Oct. 12, 2006, 4 pgs.
Office Action dated Jan. 5, 2007, U.S. Appl. No. 11/546,303, filed Oct. 12, 2006, 7 pgs.
Response dated Jul. 5, 2007, U.S. Appl. No. 11/546,303, filed Oct. 12, 2006, 6 pgs.
Examiner's Search Strategy dated Mar. 10, 2005, U.S. Appl. No. 11/546,303, filed Oct. 12, 2006, 36 pgs.
Examiner's Interview Summ. dated Jan. 17, 2008, U.S. Appl. No. 11/546,304, filed Oct. 12, 2006 now U.S. Pat. No. 7,420,057 issued Sep. 2, 2008, 3 pgs.
Notice of Allowance dated Apr. 30, 2008, U.S. Appl. No. 11/546,304, filed Oct. 12, 2006 now U.S. Pat. No. 7,420,057 issued Sep. 2, 2008, 8 pgs.
Office Action dated Jan. 3, 2007, U.S. Appl. No. 11/546,304, filed Oct. 12, 2006 now U.S. Pat. No. 7,420,057 issued Sep. 2, 2008, 7 pgs.
Office Action dated Jul. 18, 2007, U.S. Appl. No. 11/546,304, filed Oct. 12, 2006 now U.S. Pat. No. 7,420,057 issued Sep. 2, 2008, 4 pgs.
Response dated Jan. 17, 2008, U.S. Appl. No. 11/546,304, filed Oct. 12, 2006 now U.S. Pat. No. 7,420,057 issued Sep. 2, 2008, 24 pgs.
Response dated Apr. 3, 2007, U.S. Appl. No. 11/546,304, filed Oct. 12, 2006 now U.S. Pat. No. 7,420,057 issued Sep. 2, 2008, 7 pgs.
Supp. Response dated Mar. 19, 2008, U.S. Appl. No. 11/546,304, filed Oct. 12, 2006 now U.S. Pat. No. 7,420,057 issued Sep. 2, 2008, 13 pgs.
Supp. Response dated Mar. 24, 2008, U.S. Appl. No. 11/546,304, filed Oct. 12, 2006 now U.S. Pat. No. 7,420,057 issued Sep. 2, 2008, 14 pgs.
2nd Supp. Response dated Apr. 23, 2008, U.S. Appl. No. 11/546,304, filed Oct. 12, 2006 now U.S. Pat. No. 7,420,057 issued Sep. 2, 2008, 14 pgs.
Final Office Action dated Apr. 23, 2007, U.S. Appl. No. 11/079,070, filed Mar. 14, 2005, 11 pgs.
Notice of Allowance dated Sep. 14, 2007, U.S. Appl. No. 11/079,070, filed Mar. 14, 2005, 6 pgs.
Office Action dated Jan. 11, 2008, U.S. Appl. No. 11/079,070, filed Mar. 14, 2005, 8 pgs.
Office Action dated Sep. 13, 2006, U.S. Appl. No. 11/079,070, filed Mar. 14, 2005, 5 pgs.
Response to Final Office Action dated Jul. 23, 2007, U.S. Appl. No. 11/079,070, filed Mar. 14, 2005, 7 pgs.
RCE dated Nov. 2, 2007, U.S. Appl. No. 11/079,070, filed Mar. 14, 2005, 4 pgs.

(56) References Cited

OTHER PUBLICATIONS

Response dated Jan. 16, 2007, U.S. Appl. No. 11/079,070, filed Mar. 14, 2005, 8 pgs.
Examiner Search Strategy dated Jan. 3, 2008, U.S. Appl. No. 11/079,070, filed Mar. 14, 2005, 20 pgs.
Examiner's Search Strategy dated Jul. 21, 2006, U.S. Appl. No. 11/079,070, filed Mar. 14, 2005, 106 pgs.
Advisory Action dated Jul. 2, 2009, U.S. Appl. No. 11/278,551, filed Apr. 4, 2006, 3 pgs.
Final Office Action dated Apr. 13, 2009, U.S. Appl. No. 11/278,551, filed Apr. 4, 2006, 9 pgs.
Office Action dated Jun. 1, 2007, U.S. Appl. No. 11/278,551, filed Apr. 4, 2006, 9 pgs.
Office Action dated Jul. 6, 2006, U.S. Appl. No. 11/278,551, filed Apr. 4, 2006, 8 pgs.
Office Action dated Jul. 9, 2008, U.S. Appl. No. 11/278,551, filed Apr. 4, 2006, 12 pgs.
Office Action dated Dec. 28, 2009, U.S. Appl. No. 11/278,551, filed Apr. 4, 2006, 9 pgs.
Responsive Amendment to Final Office Action, dated Jun. 12, 2009, U.S. Appl. No. 11/278,551, filed Apr. 4, 2006, 63 pgs.
RCE and Responsive Amendment to Final Office Action, dated Oct. 7, 2009, U.S. Appl. No. 11/278,551, filed Apr. 4, 2006, 14 pgs.
Response dated Jan. 9, 2009, U.S. Appl. No. 11/278,551, filed Apr. 4, 2006, 64 pgs.
Response dated Nov. 30, 2007, U.S. Appl. No. 11/278,551, filed Apr. 4, 2006, 25 pgs.
Response dated Dec. 19, 2006, U.S. Appl. No. 11/278,551, filed Apr. 4, 2006, 4 pgs.
Examiner's Search Strategy dated Apr. 13, 2009, U.S. Appl. No. 11/278,551, filed Apr. 4, 2006, 2 pgs.
Examiner's Search Strategy dated Jun. 1, 2007, U.S. Appl. No. 11/278,551, filed Apr. 4, 2006, 10 pgs.
Examiner's Search Strategy dated Jun. 26, 2006, U.S. Appl. No. 11/278,551, filed Apr. 4, 2006, 19 pgs.
Examiner's Search Strategy dated Jul. 9, 2008, U.S. Appl. No. 11/278,551, filed Apr. 4, 2006, 6 pgs.
Examiner's Search Strategy dated Dec. 28, 2009, U.S. Appl. No. 11/278,551, filed Apr. 4, 2006, 3 pgs.
Final Office Action dated Sep. 12, 2008, U.S. Appl. No. 11/381,590, filed Apr. 4, 2006, 10 pgs.
Office Action dated Apr. 3, 2007, U.S. Appl. No. 11/381,590, filed Apr. 4, 2006, 8 pgs.
Office Action dated Dec. 27, 2007, U.S. Appl. No. 11/381,590, filed Apr. 4, 2006, 8 pgs.
Response dated Jun. 26, 2008, U.S. Appl. No. 11/381,590, filed Apr. 4, 2006, 7 pgs.
Amendment and Reply dated Oct. 3, 2007, U.S. Appl. No. 11/381,590, filed Apr. 4, 2006, 8 pgs.
Examiner's Search Strategy dated Mar. 30, 2007, U.S. Appl. No. 11/381,590, filed Apr. 4, 2006, 48 pgs.
Office Action dated Mar. 23, 2009, U.S. Appl. No. 11/383,796, filed May 17, 2006; 11 pgs.
Examiner's Search Strategy dated Mar. 23, 2009, U.S. Appl. No. 11/383,796, filed May 17, 2006; 2 pgs.
Office Action dated Mar. 19, 2009, U.S. Appl. No. 11/383,793, filed May 17, 2006, 12 pgs.
Examiner's Search Strategy dated Mar. 19, 2009, U.S. Appl. No. 11/383,793, filed May 17, 2006, 3 pgs.
Doelker et al., Physicochemical behavior or active substances. Consequences for the feasibility and stability of pharmaceutical forms, S.T.P. Pharma Pratiques, 1990, 9(5):399-409.
Doelker et al., Crystalline modifications and polymorphism changes during drug manufacturing, Annales Pharmaceutiques Francaises, 2002, 60(3):161-169.
Engelson, Concise Encyclopedia Chemistry, 1993, pp. 872-873.
Jain et al., Indian Drugs, 1986, 23(6):315-329.
Mutschler et al., The Effect of Drugs: Antidepressive Agents, Manual of Pharmacology and Toxicology, 2001, 8th Ed, pp. 171-172, Scientific Publishing Company PLC, Stuttgart.
Muzaffar et al., J. Pharmacy, 1979, 1(1):59-66.
Porter, Remingtons, 1990, Chpt 90, pp. 1666-1675.
Rapkin, General Gynecology, 2007, 196:97-106.
Rubenstein, Pharmaceutics: The Science of Dosage Form Design, ed. Aulton, 1988, pp. 304-321.
Stearns et al., J. of Clin. Oncology, 2002, 20(6):1436-1438.
Stedman's Medical Dictionary definition "Prevention," 2000, 28th ed., 3 pgs., Lippincott Williams & Wilkins.
Clayton et al., Validation of the Decreased Sexual Screener (DSDS): a Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).
Wunderlich et al., Using e-Diaries to Measure Sexual Desire in Women with Hypoactive Sexual Desire Disorder, International Society for the Study of Womens Sexual Health (ISSWSH) annual meeting, 2007, 11 pgs. (Oral Presentation).
Clayton et al., Validation of the Sexual Interest and Desire Inventory-Female (SIDI-F) in North American Women, International Society for the Study of Womens Sexual Health (ISSWSH) annual meeting, 2007, 3 pgs. (poster and abstract).
Clayton et al., Validity of Sexual Distress Scales vs Electronic Diary in Women with Decreased Sexual Desire , American College of Obstetrics and Gynecologiest (ACOG) annual meeting, 2007,Supplement in Obstetrics and Gynecology, 1 pg. (abstract only).
Clayton et al., Validating the Sexual Insterest and Desire Inventory (SIDI-F) in North American Women , American College of Obstetrics and Gynecologists (ACOG) annual meeting, 2007, 1 pg. (abstract only).
Clayton et al., Validation of the Sexual Interest and Desire Inventory-Female (SIDI-F) in North American Women, American Psychiatric Association (APA) annual meeting, 2007, 2 pgs. (poster and abstract).
Tignol et al., Using e-Diaries to Measure Sexual Desire in Women with Hypoactive Sexual Desire Disorder, European Society for Sexual Medicine (ESSM) annual meeting, 2007, 9 pgs. (oral presentation).
Clayton, Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 10 pgs. (oral presentation).
Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/ISSM) 2008, 1 pgs. (abstract).
Clayton et al., Baseline characteristics of patients enrolled in three Phase III North American trials of flibanserin in premenopausal women with Hypoactive Sexual Desire Disorder, International Society for the Study of Womens Sexual Health (ISSWSH) annual meeting 2009, poster, 2 pgs. (poster and abstract).
Clayton et al., Validation of the Decreased Sexual Desire Screener (DSDS): A Brief Diagnostic Instrument for Generalized Acquired Female Hypoactive Sexual Desire Disorder (HSDD): J. Sex Med., 2009, pp. 1-9. (epub ahead of print).
Dean, Decreased Sexual Desire Screener© (DSDS©) for Diagnosis of Hypoactive Sexual Desire Disorder in Women, WONCA Europe conference, 2008, 8 pgs. (oral presentation).
Dean et al., Decreased Sexual Desire Screener© (DSDS©) for Diagnosis of Hypoactive Sexual Desire Disorder in Women, WONCA Europe conference, 2008, 1 pg. (abstract).
Derogatis et al., Validation of Sexual Distress Scales and Electronic Diary in Women with Hypoactive Sexual Desire Disorder, International Society for the Study of Womens Sexual Health (ISSWSH) annual meeting, 2007, 3 pgs. (poster and abstract).
Derogatis et al., Validation of Sexual Distress Scales and Electronic Diary in Women with Hypoactive Sexual Desire Disorder. American Psychiatric Association (APA) annual meeting, 2007, 2 pgs. (poster and abstract).
Derogatis et al., Content Validity of the Female Sexual Distress Scale-Revised (FSDS-R) in Women with Hypoactive Sexual Desire

(56) References Cited

OTHER PUBLICATIONS

Disorder (HSDD), Joint Congress of the European and International Societies of Sexual Medicine (ESSM/ISSM) 2008, 5 pgs. (poster, oral presentation and abstract).
Derogatis et al., Validation of the Female Sexual Distress Scale Revised (FSDS-R) for assessing distress in women with Hypoactive Sexual Desire Disorder (HSDD), J Sex Med., 2008, 5:357-364.
Dennerstein et al., Differentiating Four Cognitive-Behavioral Types of Women with Low Sexual Desire, International Society for the Study of Womens Sexual Health (ISSWSH) annual meeting, 2007, 9 pgs. (Oral Presentation).
Anonymous, Hormone Patch may Provide Some Increase in Sexual Desire in Menopausal Women, Jul. 25, 2005, URL:http://pubs.ama-assn.org/media/2005a/0725.dtl.
Bechard, et al., Int. J. Phar., 1992, 87:133-139.
Braiman, Psychosexual disorders of young adulthood, Clin Obstetrics and Gynecology, 1970, 13(3):734-745.
Byrn, et al., Hydrates and Solvates, Solid State Chemistry & Drugs, 1999, Chpt. 11, pp. 233-247.
Buhrich, et al., Can fetishism occur in transexuals?, Arch Sex Behav, 1977, 6(3):223-235.
Butts, The relationship between sexual addiction and sexual dysfunction, J. Health Care Underserved, 1992, 3(1):128-35; discussion 136-7.
Buvat, et al., Role of hormones in sexual dysfunction, homosexuality, transexualism, and paraphilia related disorders, Diagnostic and therapeutic consequences, Contracept Fertil Sex, 1996, 24(11):834-846—only English abstract.
Bymaster, et al., Fluoxetine, but not other selective serotonin uptake inhibitors, increases norepinephrine and dopamine extracellular levels in prefrontal cortex, Psychopharmacology, 2002, 160:353-361.
Chiao, et al., Remington Pharm 19$^{th}$ Ed., Panamerican Spain, 1988, pp. 2535-2537.
Cooper et al., A female sex offender with multiple paraphilias: a psychologic, physiol ogic (laboratory sexual arousal) and endocrine case study, Can J Psychiatry, 1990, 35(4):334-7.
Grau, et al., Risk Factors, Outcome, and Treatment in Subtypes of Ischemic Stroke: The German Stroke Data Bank, Stroke, 2001; 32:2559-2566.
Guarraci, et al: Coffee, Tea and Me: Moderate doses of caffine affect sexual behavior in female rats, Pharma Biochem and Behavior, Nov. 2005, 82(3):522-530. ISSN: 0091-3057 Elsevier, US, abstract.
Kafka, A Monoamine Hypothesis for the Pathophysiology of Paraphilic Disorders, Archives of Sex Behav, 1997, 26(4):343-58.
Marshall, et al., Unified Approach to the Analysis of Genetic Variation in Serotonergic Pathways, Am J. Med. Genetics Neurophychiatric Genetics, 1999, 88:621-627.
Moser, Lust, lack of desire and paraphilias: some thoughts and possible connections, Marital Ther, 1992, 18(1):65-9.
Mutschler, et al., The Effect of Drugs: Antidepressive Agents, Manual of Pharmacology and Toxicology, 8th Ed, pp. 171-172, Scientific Publishing Company PLC, Stuttgart.
Otsuka, et al., Chem. Pharm. Bull., 1999, 47(6):852-856.
Pharmacopia, 1995, p. 1843.
Schwartz, et al., Conceptual factors in the treatment of paraphilias: a preliminary rep., Martial Ther, 1983, 9(2):3-18.
Semkova, et al., Neuroprotective effect of 5-HT1A receptor agonist, Bay x 3702, demonstrated in vitro and in vivo, Euro J Pharm, 1998, 359:251-260.
Singhal, et al., Advanced Drug Delivery Reviews, 2004, 56:335-347.
Soederberg, et al., Leptin is a Risk Marker for First-Ever Hemorrhagic Stroke in a Population-Based Cohort, Stroke, Jl of the Am Heart Assoc., 1999, 30:328-337.
Stedman's Medical Dictionary definition "Anxiety", 28$^{th}$ Ed., 2006, p. 114, Lippincott Williams & Wilkins, Baltimore MD.
Thrombolytic Therapy: MedlinePlus Medical Encylopedia, http://www.nlm.nih.gov/medlineplus/ency/article/007089.htm, accessed Dec. 17, 2009, pp. 1-4.

Vippagunta, Acv. Drug Del. Rev., 2001, 48:3-26.
Welsh, et al., Effect of Lactacidosis on Pyridine Nucleotide Stability During Ischemia in Mouse Brain, J Neurochemistry, 1987, 49(3):846-851.
Zverina, et al., The occurrence of atypical sexual experience among various female groups, Arch Ses Behav, 1987, 16(4):321-6.
Clinical Study Description, http:...clinicaltrials.gov/ct2/show/NCT00832065.
Atypical Sexual Behavior During Sleep, Psychosomatic Medicine 64:328-336 (2002).
Sexsomnia, http://lakesidepress.com/pulmonary/Sleep/sexsomnia.html.
Office Action dated Aug. 20, 2008 in U.S. Appl. No. 11/097,939.
Office Action dated Jul. 9, 2008 in U.S. Appl. No. 11/278,551.
Office Action dated Jul. 18, 2008 in U.S. Appl. No. 11/381,130.
Response dated Jun. 26, 2008 in U.S. Appl. No. 11/381,590.
Office Action dated Sep. 12, 2008 in U.S. Appl. No. 11/381,590.
Office Action dated Aug. 18, 2008 in U.S. Appl. No. 11/740,959.
Office Action dated May 23, 2007 in U.S. Appl. No. 11/364,153.
Response dated Sep. 24, 2007 in U.S. Appl. No. 11/364,153.
Office Action dated Nov. 29, 2007 in U.S. Appl. No. 11/364,153.
Response dated May 29, 2008 in U.S. Appl. No. 11/364,153.
Office Action dated Sep. 4, 2008 in U.S. Appl. No. 11/364,153.
U.S. Appl. No. 12/170,884, filed Jul. 10, 2008, Bombarda et al.
Pyke et al., "Flibanserin: A Novel Centrally Acting Agent that is not an Effective Antidepressant but has Potential to Treat Decreased Sexual Desire in Women," May 2008 (poster).
Pyke et al., "Flibanserin: A Novel Centrally Acting Agent that is not an Effective Antidepressant but has Potential to Treat Decreased Sexual Desire in Women," May 2008 (abstract).
Konarski et al., "Effects of Acute Flibanserin on FDG-PET Brain Glucose Metabolism in Men with Major Depressing Disorder," Aug. 2008 (poster).
Konarski et al., "Effects of Acute Flibanserin on FDG-PET Brain Glucose Metabolism in Men with Major Depressive Disorder," Aug. 2008 Barcelona meeting of the European College of Neuropsychopharmacology (abstract).
Stoleru, et al., "Brain processing of visual sexual stimuli in men with hypoactive sexual desire disorder," Psychiatry Res.: Neuroimaging 124 (2003) 67-86.
Clayton, et al., "Prevalence of Sexual Dysfunction Among Newer Antidepressants," J. Clin. Psychiatry 63:4 (2202) 357-366.
Kennedy, et al., "Sexual dysfunction before antidepressant therapy in major depression," J. Affective Disorders 56 (1999) 201-208.
Goldfischer, et al., Selected 2008 Abstracts from the International Society for the Study of Women's Sexual Health, J. Sex. Med. 2008; 5 (suppl. 3) pp. 159.
Goldfischer, et al., Selected 2008 Abstracts from the International Society for the Study of Women's Sexual health, J. Sex. Med. 2008; 5 (suppl. 3) pp. 159-160.
Backhauß, et al., "A Mouse Model of Focal Cerebral Ischemia for Screening Neuroprotective Drug Effects," Journal of Pharmacological Methods 27, 27-32 (1992).
Fujikura, et al., "Effects of naftidrofuryl oxalate, a 5-HT$_2$ antagonist, on neuronal damage and local cerebral blood flow following transient cerebral ischemia in gerbils," Brain Research 636 (1994) 103-106.
Prehn, et al., "Neuroprotective properties of 5-HT$_{1A}$ receptor agonists in rodent models of focal and global cerebral ischemia," European Journal of Pharmacology 203 (1991) 213-222.
Prehn, et al., "Effects of serotonergic drugs in experimental brain ischemia: evidence for a protective role of serotonin in cerebral ischemia," Brain Research 630 (1993) 10-20.
Shibata, et al., "Ischemia-induced impairment of 2-deoxyglucose uptake and CAI field potentials in rat hippocampal slices: protection by 5-HT$_{1A}$ receptor agonists and 5-HT$_2$ receptor antagonists," European Journal of Pharmacology, 229 (1992) 21-29.
New Collegiate Dictionary 1981, p. 311 (definition of term "diagnosis").
"Types of Back Pain: Acute Pain, Chronic Pain, and Neuropathic Pain," Spine-health.com, www.spine-health.com/topics/ed/chronicpain02.html, (Oct. 2, 2007).

(56) References Cited

OTHER PUBLICATIONS

Gonzales, S., "Natural Compound May Offer New Treatment for Chronic Pain," NIDA Notes, vol. 16, No. 3—Aug. 2001, www.nida.nih.gov/NIDA_Notes/NNVol16N3/Natural.htm.
Miranda, et al., "Dexketoprofen-Induced antinociception in animal models of acute pain: Synergy with morphine and paracetamol," Neuropharmacology 52(2007) 291-296.
Okamoto, et al., "5-HT2A receptor subtype in the peripheral branch of sensory fibers is involved in the potentiation of inflammatory pain in rats," Pain 99 (2002) 133-143.
Roseland, et al., "The formalin test in mice: effect of formalin concentration," Pain 42 (1990) 235-242.
Frampton, et al., "Pentoxifylline (oxpentifylline): A Review of its Therapeutic Efficacy in the Management of Peripheral Vascular and Cerebrovascular Disorders," Drug Evaluation, Drugs and Aging 7(6), pp. 480-503 (1995).
Borsini, et al., "BIMT 17: a putative antidepressant with a fast onset of action?" Psychopharmacology (1977) 134:378-386.
U.S. Appl. No. 11/956,949, filed Dec. 14, 2007, D. Lewis-D'Agostino et al.
U.S. Appl. No. 11/997,567, filed Feb. 1, 2008, Ceci.
ISR PCT/EP 02/11103—WO 03/035072.
Request for Continued Examination filed Nov. 2, 2007 in U.S. Appl. No. 11/079,070.
Office Action dated Jan. 11, 2008 in U.S. Appl. No. 11/079,070.
Office Action dated Apr. 14, 2006 in U.S. Appl. No. 11/178,716.
Response dated Jul. 25, 2006 in U.S. Appl. No. 11/178,716.
Office Action dated Jan. 26, 2007 in U.S. Appl. No. 11/178,716.
Restriction Requirement dated Sep. 11, 2003 in U.S. Appl. No. 10/214,781.
Response to Restriction Requirement filed Sep. 22, 2003 in U.S. Appl. No. 10/214,781.
Office Action dated Jan. 5, 2004 in U.S. Appl. No. 10/214,781.
Office Action dated Oct. 11, 2005 in U.S. Appl. No. 10/882,613.
Office Action dated Aug. 15, 2006 in U.S. Appl. No. 11/218,107.
Response dated Feb. 14, 2007 in U.S. Appl. No. 11/218,107.
Office Action dated May 18, 2007 in U.S. Appl. No. 11/218,107.
Office Action dated Jul. 6, 2006 in U.S. Appl. No. 11/278,551.
Response dated Dec. 19, 2006 in U.S. Appl. No. 11/278,551.
Office Action dated Jun. 1, 2007 in U.S. Appl. No. 11/278,551.
Response dated Nov. 30, 2007 in U.S. Appl. No. 11/278,551.
Supplemental Response dated Dec. 3, 2007 in U.S. Appl. No. 11/278,551.
Office Action dated Oct. 9, 2007 in U.S. Appl. No. 11/381,130.
Response dated Apr. 9, 2008 in U.S. Appl. No. 11/381,130.
Office Action dated Apr. 3, 2007 in U.S. Appl. No. 11/381,590.
Response dated Oct. 3, 2007 in U.S. Appl. No. 11/381,590.
Office Action dated Dec. 27, 2007 in U.S. Appl. No. 11/381,590.
U.S. Appl. No. 12/091,848, filed Apr. 28, 2008, Ceci, et al.
U.S. Appl. No. 10/272,603, filed Dec. 19, 2006, Borsini et al.
U.S. Appl. No. 11/079,070, filed Jul. 21, 2005, Bombarda et al.
U.S. Appl. No. 11/364,153, filed Sep. 21, 2006, Pyke et al.
U.S. Appl. No. 11/546,303, filed Feb. 8, 2007, Bombarda et al.
U.S. Appl. No. 11/546,304, filed Feb. 8, 2007, Bombarda et al.
U.S. Appl. No. 11/550,869, filed May 31, 2007, Ceci.
U.S. Appl. No. 11/837,957, Eisenreich et al.
U.S. Appl. No. 11/837,959, Eisenreich et al.
U.S. Appl. No. 11/837,962, Pearnchob et al.
U.S. Appl. No. 60/348,911, Borsini et al.
U.S. Appl. No. 60/658,551, Pyke.
U.S. Appl. No. 60/658,566, Pyke.
U.S. Appl. No. 60/658,611, Pyke.
U.S. Appl. No. 60/734,405, Pyke et al.
Archer, T. "5HT, Pain and Anxiety," Behavioural Pharmacology of 5-HT (1989), pp. 299-300.
Awouters et al. "Oxatomide, a new orally active drug which inhibits both the release and the effects of allergic mediators." Chemical Abstracts, vol. 88, No. 15, 88:98788c (Apr. 10, 1978).

Basson et al. "Report of the International Concensus Development Conference on Female Sexual Dysfunction: Definitions and Classifications." The Journal of Urology, vol. 163 (Mar. 2000), pp. 888-893.
Baxter, G., "5-HT2 Receptor Subtypes: a family re-united?", Trends in Pharmacological Sciences, Elsevier, Haywarth, GB, vol. 16, No. 3, Mar. 1995, pp. 105-110.
Beers et al., ed. The Merck Manual of Diagnosis and Therapy, 17th ed. (1999), pp. 1595-1598.
Bernstein, J. et al. "Concomitant Polymorphs." Angewandte Chemise, Int. Ed. (1999), pp. 3441-3461.
Bevan et al. "5-HT and Sexual Behaviour." Behavioural Pharmacology of 5-HT, pp. 33-34, 87-88 (1989).
Borsini et al., Flibanserin, Drugs of the Future, 23(1):9-16 (1998).
Borsini et al., Behavioral Effects of Flibanserin (BIMT 17), Sep. 1999, Pharmacology Biochemistry and Behavior, vol. 64, Issue 1, pp. 137-146.
Borsini, et al., "Lack of interaction between flibanserin and antidepressants in inducing serotonergic syndrome in rats." International Journal of Neuropsychopharmacology 4(1): 9-15 (2001).
Borsini, et al., "Mechanism of action of flibanserin in the learned helplessness paradigm in rats," European Journal of Pharmacology 433: 81-89 (2001).
Borsini, et al., "Pharmacology of Flibanserin" CNS Drug Reviews 2002: vol. 8, No. 2, pp. 117-142.
Borsini, F. et al. "BIMT-17, a 5HT-2A Receptor Antagonist and 5HT-1A Receptor Full Agonist in Rat Cerebral Cortex," Naunyn-Schmiedeberg's Archives of Pharm., 352(3):276-82 (1995).
Brambilla, et al., "Effect of flibanserin (BIMT 17), fluoxetine, 8-)H-DPAT and buspirone on serotonin synthesis in rat brain," European Neuropsychopharmacology 10(1): 63-67 (1999).
Carey, John, "Viagra for Women?" BusinessWeek.com (Dec. 28, 2006).
Cesana, et al., "The effect of BIMT 17, a new potential antidepressant, in the forced swimming test in mice," Behavioural Pharmacology 6: 688-94 (1995).
Chalmers et al. "Corticotrophin-releasing Factor Receptors: from Molecular Biology to Drug Design." TIPS vol. 17 (Apr. 1996), pp. 166-172.
Cloninger, C. R. "A Systematic Method for Clinical Description and Classification of Personality Variants," Arch. Gen. Psychiatry, vol. 44 (Jun. 1987), pp. 573-588.
Collino, F. et al. Chemical Abstract: Database Accession No. 98:16650-XP 002197885: Mannich bases of benzimidazoles, benzotriazoles and other analogous compounds, with pharmacological activity.
Cools, A. R. "Depression and Psychosis," Behavioural Pharmacology of 5-HT (1989), pp. 153-155.
Cremers et al., "Non Erectile Dysfunction Application of Sildenafil", Herz, vol. 28, No. 4, pp. 325-333, 2003.
Crook, T. & Lakin, M. "Effects of Ondansetron in Age-associated Memory Impairment." The role of ondansetron, a novel 5-HT3 antagonist, in the treatment of psychiatric disorders, 5th World Congress of Biochemical Psychiatry, pp. 21-23 (1991).
Cyr et al. "Nefazodone: Its Place among Antidepressants." Annals of Pharmacotherapy 30(9): 1006-12 (1996).
Damit et al., "Hemodynamic effects of pharmacological block during acute overload of the heart" Database accession # 1978:591197 XP-002436715.
Damour et al. "Preparation and formulation of I-[(4-phenyl-piperazino)alkyl]benzimidazolin-2-ones and analogs as serotonin S2 antagonists." Chemical Abstracts, vol. 118, No. 13, 118:124537e (Mar. 29, 1993).
Darlington, C. "Flibanserin." Current Opinion in CPNS Investigational Drugs, 1(4): 510-13 (1999).
De Angelis, "5-HT2A antagonist in psychiatric disorders." Current Opinion in Investigational Drugs. vol. 3, N.R. 1, pp. 106-112 (2002).
De Vry, J. "5-HT1A receptors in psychopathology and the mechanism of action of clinically effective therapeutic agents." Drug News and Perspectives 9(5): 270-80 (1996).

(56) References Cited

OTHER PUBLICATIONS

Dimmock, P. et al. "Efficacy of Selective Serotonin-Reuptake Inhibitors in Premenstrual Syndrome: A Systematic Review." The Lancet, vol. 356, No. 9236 (Sep. 30, 2000), pp. 1131-1136.
Fourcroy, Jean L. "Female Sexual Dysfunction: Potential for Pharmacotherapy." Drugs, vol. 63, No. 14 (2003), pp. 1445-1457.
Geyer, M. "5-HT2 Antagonists Increase Tactile Startle Habituation in an Animal Model of Habituation Deficit in Schizophrenia." Behavioural Pharmacology of 5-HT, pp. 243-246 (1989).
Giron, D. "Thermal Analysis and Calorimetric Methods in the Characterization of Polymorphs and Solvates." Thermochimica ACTA, Elsevier Science, 248 (1995), pp. 1-59.
Goa et al. "Buspirone: A preliminary review of its pharmacological properties and therapeutic efficacy as an anxiolytic." Drugs 32:114-29 (1986).
Gould, "Salt Selection for Basic Drugs." International Journal of Pharmaceutics vol. 33, Issues 1-3 (Nov. 1986), pp. 201-217.
Greene, T. "Protective Groups in Organic Synthesis." Havard University (Wiley-Interscience Publication. 1981), pp. 10-17.
Hansenne, M. et al. "Harm avoidance dimension of the tridimensional personality questionnaire and serotonin-I A activity in depressed patients." Biol. Psychiatry 42: 959-61 (1997).
Invernizzi et al. "Flibanserin, a Potential Antidepressant Drug, Lowers 5-HT and Raises Dopamine and Noradrenaline in the Rat Prefrontal Cortex Dialysate: Role of 5-HT1A Receptors." British Journal of Pharmacology, vol. 139 (Jun. 2003), pp. 1281-1288.
Kleven, M., "Modification of behavioral effects of 8-hydroxy-2-(di-n-propylamino) tetralin following chronic ethanol consumption in the rat: evidence for the involvement of 5-HT1A receptors in ethanol dependence.", European Journal of Pharmacology, 1995, vol. 281, No. 3, pp. 219-228.
Koba, "Involvement of peripheral 5-HT2A receptor activation in pain behaviour evoked by formalin paw injection in the rat," Kyushu Shika Gakkai Zaahi 53(1): 253-60 (1999).
Lammers G.J. et al. "Ritanserin, a 5-HT2 receptor blocker, as add-on treatment in narcolepsy," Sleep 14(2): 130-32 (1991).
Leonard, B. E. "Sub-types of Serotonin Receptors: Biochemical Changes and Pharmacological Consequences," International Clinical Psychopharmacology 7: 13-21 (1992).
Lyrer, "Neue Ansatze in der Akutbehandlung des zerebrovaskutaren Insultes." Schweiz. Med. Wochenschr., vol. 124, No. 45 (1994), pp. 2005-2012.
Marazziti, et al., "Region-dependent effects of flibanserin and buspirone on adenylyl cyclase activity in the human brain," Int'l Journal of Neuropsychopharmacology 5(2): 131-40 (Jun. 2002).
Martindale, "Anxiolytic Sedatives Hypnotics and Antipsychotics," The Complete Drug Reference, p. 635 (1999).
McCall, R.B. et al. "Role of serotinin1A and serotonin2 receptors in the central regulation of the cardiovascular system." Pharmacological Reviews 46(3): 231-43 (1994).
"Merck Manual of diagnosis and therapy", Merck Research Laboratories, USA 1999, p. 1410, col. 1—p. 1413, col. 2, paragraph 1: p. 1412, tables 173-2 XP-002439435.
Moynihan, R., "The making of disease: female sexual dysfunction" British Medical Journal, 2003, vol. 326, pp. 45-47.
Nadeson, et al., "Antinoceptive role of 5-HT1A receptors in rat spinal cord," British Journal of Anaesthesia 88(5): 679-84 (2002).
Petkov, V.D. et al. "Participation of different 5-HT receptors in the memory process in rats and its modulation by the serotonin depletor p-chlorophenylalanine." Acta Neurobiol. Exp. 55: 243-52 (1995).
Podhorna et al. "Flibanserin has Anxiolytic Effects without Locomotor Side Effects in the Infant Rat Uultrasonic Vocalization Model of Anxiety." British J. of Pharm., vol. 130, No. 4 (2000), pp. 739-746.
Reikkinen et al. "The Effects of Increased Serotonergic and Decreased Cholinergic Activities on Spatial Navigation Performance in Rats." Pharmacology Biochemistry & Behavior, vol. 39 (1991), pp. 25-29.

Reuter, L. E. et al. "Electrophysiological Examination of the Effects of Sustained Flibanserin Administration on Serotonin Receptors in Rat Brain." British J. of Pharm., vol. 126, No. 3 (1999), pp. 627-638.
Risch, S. Craig et al. "Neurochemical alterations of serotonergic neuronal systems in depression." J. Clin. Psychiatry 53(10) Suppl: 3-7 (1992).
Robinson, DS. "Serotonin receptor subtype and affective disorders." Clinical Neuropharmacology 16(S3): S1-S5 (1993).
Shipton, B. et al., "Valvular heart disease: review and update," American Family Physician Jun. 1, 2001, vol. 63 # 11, pp. 2201-2208.
Sietsema, D. et al., "From Taboo to Treatment?" Good Clinical Practice Journal, Jan. 2005, vol. 12, # 1, pp. 23-27.
Steiner, M. "Recognition of Premenstrual Dysphoric Disorder and its Treatment." The Lancet, vol. 356, No. 9236 (Sep. 30, 2000), pp. 1126-1127.
Vaudenberk et al. "Piperazine and Piperidine Derivatives," Chemical Abstracts, vol. 88, No. 5, 88:50920n (Jan. 30, 1978).
Walsh, K. et al., "Sexual dysfunction in the older women and overview of the current understanding and management" Drugs and Aging, 2004, vol. 21, # 10 pp. 655-675.
Zajecka et al. "Sexual Function and Satisfaction in the Treatment of Chronic Major Depression with Nefazodone, Psychotherapy, and their Combination." Journal of Clinical Psychiatry, 63(8): 709-16 (Aug. 2002).
Office action dated Jul. 26, 2004 in U.S. Appl. No. 10/210,474.
Response and declaration dated Jan. 24, 2005 in U.S. Appl. No. 10/210,474.
Reply with Amendment in response to telephone interview of Mar. 8, 2005 in U.S. Appl. No. 10/210,474.
Office Action dated Mar. 16, 2005 in U.S. Appl. No. 10/210,474.
Office Communication dated Apr. 12, 2005 in U.S. Appl. No. 10/210,474.
Amendment dated Jul. 8, 2005 in U.S. Appl. No. 10/210,474.
Office Action dated Oct. 5, 2005 in U.S. Appl. No. 10/210,474.
Response dated Dec. 15, 2005 in U.S. Appl. No. 10/210,474.
Applicant Initiated Interview Request Form dated Jan. 13, 2006 in U.S. Appl. No. 10/210,474.
Supplemental Amendment dated Jan. 19, 2006 in U.S. Appl. No. 10/210,474.
Notice of Allowance and Notice of Allowability dated Jan. 30, 2006 in U.S. Appl. No. 10/210,474.
Notice of Allowance and Notice of Allowability dated Jul. 12, 2006 in U.S. Appl. No. 10/210,474.
Office Action dated Sep. 13, 2006 in U.S. Appl. No. 11/079,070.
Response to Office Action dated Jan. 16, 2007 in U.S. Appl. No. 11/079,070.
Office Action dated Apr. 23, 2007 in U.S. Appl. No. 11/079,070.
Response to Office Action dated Jul. 23, 2007 in U.S. Appl. No. 11/079,070.
Notice of Allowance and Notice of Allowability dated Sep. 14, 2007 in U.S. Appl. No. 11/079,070.
Office Action dated Jul. 2, 2007 in U.S. Appl. No. 11/110,449.
Office Action dated Dec. 6, 1994 in U.S. Appl. No. 08/216,742.
Amendment dated Jun. 6, 1995 in U.S. Appl. No. 08/216,742.
Office Action dated Oct. 16, 1995 in U.S. Appl. No. 08/216,742.
Amendment dated Apr. 8, 1996 in U.S. Appl. No. 08/216,742.
Supplemental Amendment dated Apr. 25, 1996 in U.S. Appl. No. 08/216,742.
Notice of Allowance and Allowability dated May 30, 1996 in U.S. Appl. No. 08/216,742.
Aizenberg, D. et al., "Cyproheptadine Treatment of Sexual Dysfunction Induced by Serotonin Reuptake Inhibitors" Clinical Neuropharmacology, vol. 18, No. 5 (1995), pp. 320-324.
Meston, C & B. Gorzalka,"Psychoactive Drugs and Human Sexual Behavior: The Role of Serotonergic Activity", Journal of Psychoactive Drugs, vol. 24(1), Jan-Mar. 1992, pp. 1-40.
Phillips, R. & J. Slaughter, "Depression and Sexual Desire", American Family Physician, vol. 62, No. 4 (Aug. 15, 2000).
Response filed Jan. 25, 2013 in counterpart Canadian Patent Application No. 2,617,546, 17 pages.

(56) References Cited

OTHER PUBLICATIONS

Response filed Feb. 7, 2013 in counterpart Canadian Patent Application No. 2,563,743, 15 pages.
Response filed Feb. 20, 2013 in counterpart Canadian Patent Application No. 2,626,134, 7 pages.
Response filed Feb. 20, 2013 in counterpart Canadian Patent Application No. 2,626,797, 8 pages.
Response filed Aug. 24, 2012 in counterpart Brazilian Patent Application No. PI0311169-0, 13 pages [Portuguese-language only].
Response filed Sep. 6, 2012 in counterpart European Patent Application No. 07767338.8, 4 pages.
Response filed Feb. 17, 2012 in counterpart European Patent Application No. 09774901.4, 7 pages.
Response filed Apr. 17, 2012 in counterpart European Patent Application No. 07728833.0; 19 pages.
Response filed Apr. 30, 2012 in counterpart Brazilian Patent Application No. PI0211601-4, 12 pages [Portugese language only].
Response filed Aug. 27, 2012 in counterpart Australian Patent Application No. 2006311035; 16 pages.
Response filed Sep. 12, 2012 in counterpart Australian Patent Application No. 2007247094; 23 pages.
Response filed Dec. 10, 2012 in counterpart European Patent Application No. 06764270.2, 26 pages.
Berge et al.: Pharmaceutical Salts; Journal of Pharmaceutical Sciences; Jan. 1977; vol. 66, No. 1, pp. 1-39.
Borsini et al., Flibanserin, Drugs of the Future, 1998, 23(1), pp. 9-16.
Cremers et al.; Non Erectile Dysfunction Application of Sildenafil, Herz, 2003, 23, No. 4, pp. 325-333.
Fourcroy; Female Sexual Dysfunction, Potential for Pharmacotherapy, Drugs 2003, 63 (14) pp. 1445-1457.
Hancock et al., What is the True Solubility Advantage for Amorphous Pharmaceuticals; Pharmaceutical Research, vol. 17, No. 4; 2000, pp. 397-404.
Kumar et al.; An overview of automated systems relevant in pharmaceutical salt screening, Drug Discovery Today, vol. 12, Nos. 23/24, Dec. 2007: pp. 1046-1053.
Molinoff et al.; PT-141: A Melanocortin Agonist for the Treatment of Sexual Dysfunction, Annals New York Academy of Sciences; 994; 2003; pp. 96-102.
Quirk et al., Development of a Sexual Function Questionnaire for Clinical Trails of Female Sexual Dysfunction, Journal of Women's Health & Gender-Based Medicine, vol. 11, No. 3; 2002, pp. 277-289.
Rosen et al.; The Female Sexual Function Index (FSFI): A Multi-dimensional Self-Report Instrument for the Assessment of Female Sexual Function; Journal of Sex & Martial Therapy, 26:191-208, 2006.
Salonia et al.; Sexual Dysfunction is Common in Women with Lower Urinary Tract Symptoms and Urinary Incontinence Results of a Cross-Sectional Study; European Urology 45, 2004, pp. 642-648.
Stahl et al.; Handbook of Pharmaceutical Salts Properties, Selection, and Use, pp. 211-217; International Union of Pure and Applied Chemistry (IUPAC) date unknown.
Tanaka et al.; B3-Adrenoceptor Agonists for the Treatment of Frequent Urination and Urinary Incontinence 2-[4-2{[(1S,2R}-2-Hydroxy-2-(4-hydroxyphenyl)-1-methylethyl]amino)ethyl)phenoxy]-2-methylpropionic Acid, Bioorganic & Medicinal Chemistry 9 (2001); 3265-3271.
Poster, presented Nov. 6, 2009 at Sexual Medicine Society of North American 2009 Fall Scientific Meeting, 3 pages.
Transcript of Poster, presented Nov. 6, 2009 at Sexual Medicine Society of North American 2009 Fall Scientific Meeting, "Pooled Clinical Trial Analysis of Flibanserin Safety and Tolerability in Premenopausal Women with Hypoactive Sexual Desire Disorder", 7 pages.
Semkova et al., Neuroprotective effect of 5-HT1A receptor agonist, Bay x 3702, demonstrated in vitro and in vivo 1998, European Journal of Pharmacology, vol. 359, pp. 251-260.

Prehn et al., Neuroprotective properties of 5-HT1A receptor agonists in rodent models of local and global cerebral ischemia, 1991, European Journal of Pharmacology, vol. 203, pp. 213-222.
Elger et al., Oedema reduction by levemopamil in focal cerebral ischemia of spontaneously hypertensive rats studied by magnetic resonance imaging, 1994, European Journal of Pharmacology, vol. 254, pp. 64-71.
Borsini et al., BIMT 17: a putative antidepressant with a fast onset of action? 1997, Psychopharmacology, vol. 134, pp. 378-386.
Walsh et al.; Sexual Dysfunction in the Older Women, An Overview of the Current Understanding and Management, Durgs Aging 2004, 21 (10); pp. 656-675.
Albertazzi: Noredrenergic and serotonergic modulation to treat vasomotor symptoms; J. Br. Menopause Soc., Mar. 12, 2006; (1) 7-11, Abstract.
Berman et al.; Safety and Efficacy of Sildenafil Citrate for the Treatment of Female Sexual Arousal Disorder a Double-blind, Placebo Controlled Study: The Journal of Urology Dec. 2003 vol. 170, pp. 2333-2338.
Flibanserin, from Wikipedia, 6 pages, retrieved from the Internet at http://en.wikipedia.org/wiki/Flibanserin on Jul. 3, 2012.
Ghizzani, et al.; Management of Sexual Dysfunctions in Women; J. Endorinol Invest. 26 (Suppl te No. 3) 2003, pp. 137-138.
Kaur, et al.; Prementrual Dysphoric Disorder: A Review for the Treating Practitioner Cleveland Clinic Journal of Medicine, vol. 71, No. 4, Apr. 2004; pp. 303-321.
Kroll, Treatment of Premenstrual Disorders, J. Reprod. Med., Apr. 2006, (4 Suppl)—Abstract.
Lachman et al.; The Theory and Practice of industrial Pharmacy, 3rd Edition, Lea and Fabigel Philadelphia, 1986, pp. 324-333.
Salerian et al.; Sildenafil for Psychotropic-Induced Sexual Dysfunction in 31 Women and 61 Men: Journal of Sex & Marital Therapy; 2000, 26:2, pp. 133-140.
Sietsema et al.; From Taboo to Treatment?; 2005 PJB Publications, Jan. 2005, pp. 23-27.
Gao et al., "Efficacy and Safety of Flibanserin in Women with Hypoactive Sexual Desire Disorder: A Systematic Review and Meta-Analysis", J Sex Meld, 2015, vol. 12, pp. 2095-2104.
Robinson, et al., "First Pharmacological Therapy for Hypoactive Sexual Desire Disorder in Premenopausal Women: Flibanserin", Annals of Pharmacotherapy, 2016, vol. 50(2), pp. 125-132.
Jaspers et al., "Efficacy and Safety of Flibanserin for the Treatment of Hypoactive Sexual Desire Disorder in Women: A Systematic Review and Meta-analysis", Abstract downloaded at http://www.ncbi.nlm.nih.gov/pubmed/26927498 on May 19, 2016, pp. 1-2.
Borsini et al., Behavioral Effects of Flibanserin (BIMT 17), Sep. 1999, Biochemistry and Behavior, vol. 64, Issue 1, pp. 137-146.
CMU Pharmaceutical Polymorphism, CMU Seed Fund Project on Detection and Control of Pharmaceutical Polymorphism, http://andrew.cmu.edu/user/suter/polymorph.html, as downloaded Apr. 3, 2008, 2002, pp. 1-3.
Bechard et al., Film Coating: Effect of Titanium Dioxide Concentration and Film Thickness on the Photostability of Nifedipine, International Journal of Pharmaceutics, 87 (1992), pp. 133-139.
U.S. Pharmacopia #23, 1995, pp. 1843-1844.
Borsini et al., Pharmacology of Flibanserin, 2002, CNS Drug Reviews, vol. 8, No. 2, pp. 117-142, 26 pages.
Taavoni et al., Psychogeriatrics, Hormone Replacement Therapy: Post-Menopausal Sex Life and Attitudes Towards Sex, 2005; 5:9-14, 6 pages.
Selective Serotonin Reuptake Inhibitors (SSRIs) Information; http://www.fda.gov/Drugs/DrugSafety/InformationbyDrugClass/ucm283587.htm as downloaded on Feb. 16, 2016; 2 pages.
Kurtel et al.; Journal of the American Society of Hypertension, Impaired Vasomotor Function Induced by the Combination of Hypertension and Hypercholesterolemia, 2013; 7(1) pp. 14-23,10 pages.
Menopause Practice: A Clinician's Guide 3rd edition (NAMS 2007), 7 pages.
Katz, et al.; Journal of Sex and Marital Therapy, The Relationship between Worry, Sexual Aversion, and Low Sexual Desire, 1999, vol. 25, Issue 4, abstract, 9 pages.

(56) References Cited

OTHER PUBLICATIONS

Office Action in European Patent Office in EP 09709701.8 dated Oct. 22, 2015.
Kibbe et al.; Hydroxypropyl Methylcellulose: Handbook of Pharmaceutical Excipients, 2000, 6 pages, XP-002376679.
Office Action in counterpart European Patent Application No. 07728833.0; dated Aug. 21, 2012, 5 pages.
Office Action in counterpart European Patent Application No. 06764270.2; dated Mar. 6, 2012, 4 pages.
Office Action in counterpart Australian Patent Application No. 2006311038; dated Aug. 25, 2011, 2pages.
Office Action in counterpart Australian Patent Application No. 2007247094; dated Aug. 30, 2011, 2 pages.
Office action in counterpart Brazilian Patent Application No. PI0311189-0; dated Jun. 26, 2012, 10 pages.
Office Action in counterpart European Patent Application No. 07787338.8; dated Jul. 6, 2012, 4 pages.
Office Action in commonly owned Brazilian Patent Application No. PI0213358-0; dated Jul. 24, 2015, 4 pages.
Sexual and Gender Identity Disorders, Diagnostic and Statistical Manual of Mental Disorders, Fourth Edition Text Revision, American Psychiatric Association, 2000, 34 pages, 535-566.
Katz et al.; Efficacy of Flibanserin in Women with Hypoactive Sexual Desire Disorder: Results from the Begonia Trial; J Sex Med 2013, 10, 9 pp. 1807-1815.
Singhal et al., Drug Polymorphism and Dosage Form Design: A Practical Perspective, Advanced Drug Delivery Reviews, 2004, 56 pp. 335-347.
Otsuka et al., Effect of Polymorphic Forms of Bulk Powders on Pharmaceutical Properties of Carbamazepine Granules, Chem. Pharm. Bull., 1999, 47(6) pp. 852-856.
Giron et al.: "Thermal analysis and calorimetric methods in the characterization of polymorphs and solvates" Thermochimica Acta, Elsevier Science Publishers, Amsterdam, NL, vol. 248, 1995, pp. 1-59.
Thrombolytic Therapy: MedlinePlus Medical Encyclopedia, http://www.nlm.nih.gov/medlineplus/ency/article/007089.htm, accessed Sep. 17, 2015, pp. 1-5.
Byrn, et al., Solid State Chemistry of Drugs, 1999, Chapter 11: "Hydrates and Solvates," pp. 233-247.
Walsh et al.; Sexual Dysfunction in the Older Woman, an Overview of the Current Understanding and Management; Drugs Aging 2004; 21 (10); pp. 656-675.
International Search Report for PCT/IB04/02286 dated Sep. 24, 2004.
Office Action in commonly owned Brazilian Patent Application No. 122012029907-3; dated Mar. 24, 2015, 11 pages.
Elger et al., Oedema reduction by levemopamil in focal cerebral ischemia of spontaneously hypertensive rats studied by magnetic resonance imaging, 1994, European Journal of Pharmacology, vol. 254, pp. 65-71.
Borsini et al., BIMT 17: a putative antidepressant with a fast onset of action?, Psychopharmacology, vol. 134, pp. 378-386.
Office Action in counterpart Canadian Patent Application No. 2,617,546; dated Mar. 25, 2013, 2 pages.
Vippagunta, et al., Advanced Drug Delivery Reviews, 2001; 48:3-26.
Office Action in counterpart Canadian Patent Application No. 2,626,134; dated Aug. 24, 2012, 2 pages.
Office Action in counterpart Canadian Patent Application No. 2,626,797; dated Aug. 21, 2012, 3 pages.
Office Action in commonly owned Canadian Patent Application No. 2,649,938; dated Jan. 10, 2014, 3 pages.
Office Action in commonly owned Canadian Patent Application No. 2,654,798; dated Jan. 23, 2014, 2 pages.
Office Action in commonly owned Canadian Patent Application No. 2,617,546; dated Jul. 26, 2012, 2 pages.
Borsini F et al.: "BIMT 17, a 5-HT2 Receptor Antagonist and 5-HT1A Receptor Full Agonist in Rat Cerebral Cortex" Naunyn-Schmiedeberg's Archives of Pharmacology, Springer, Berlin, DE, vol. 352, No. 3, Sep. 1995 (Sep. 1995), 7 pp. 276-282.
Office Action in commonly owned Japanese Patent Application No. 2005-530787; dated Jun. 30, 2014, 2 pages.
Office Action in commonly owned European Patent. Application No. 07728833.0; dated Apr. 9, 2013, 1 page.
Office Action in commonly owned Korean Patent Application No. 10-2008-7013699; dated Mar. 21, 2014, 5 pages.
Office Action in commonly owned Brazilian Patent Application No. PI0211601-4; dated Feb. 27, 2012 8 pages.
Office Action in commonly owned Chinese Patent Application No. 201310074677.5; dated Dec. 5, 2014, 8 pages.
Office Action in commonly owned European Patent Application No. 06807537.3; dated Mar. 8, 2013, 3 pages.
Office Action in commonly owned Canadian Patent Application No. 2,649,938; dated May 7, 2013, 3 pages.
Office Action in commonly owned Canadian Patent Application No. 2,654,798; dated May 7, 2013, 2 pages.
Office Action in commonly owned Canadian Patent Application No. 2,672,957; dated Nov. 1, 2013, 2 pages.
Office Action in counterpart Canadian Patent Application No. 2,563,743; dated Aug. 8, 2012, 2 pages.
Office Action in commonly owned Canadian Patent Application No. 2,802,600; dated Nov. 28, 2013, 2 pages.
Office Action in commonty owned Canadian Patent Application No. 2,682,015; dated Aug. 26, 2014, 2 pages.
Office Action in commonly owned Canadian Patent Application No. 2,802,600; dated Sep. 25, 2014, 2 pages.
New Collegiate Dictionary, 1981, p. 311 (i.e. definition of the term "diagnosis" as provided).
Office Action in commonly owned Korean Patent Application No. 10-2013-7033147; dated Feb. 28, 2014, 7 pages.
Office Action in commonly owned Chinese Patent Application No. 201310074677.5; dated Mar. 24, 2014, 8 pages.
Dennerstein et al.; Hypoactive Sexual Desire Disorder in Menopausal Women: A Survey of Western European Women; Journal of Sexual Medicine 2006; No. 3, 11 pages.
Leiblum et al.; Hypoactive Sexual Desire Disorder in Postmenopausal Women: US Results trom the Women's International Study of Health and Sexuality (WISHeS): Menopause: The Journal of the North American Menopause Society 2006; vol. 13, No. 1, 11 pages.
Simon et al.; Efficacy and Safety of Flibanserin in Postmenopausal Women with Hypoactive Sexual Desire Disorder: Results of the Snowdrop Trial; Menopause: The Journal of the North American Menopause Society 2013; vol. 21, No. 6, 8 pages.
Office Action in commonly owned Canadian Patent Application No. 2,699,414; dated Oct. 30, 2014, 3 pages.
Crenshaw; The Sexual Aversion Syndrome; J. Sex Marital Ther.; 1985; vol. 11, Issue 4, abstract; 1 page.
Muir et al.; Dose Optimization of Intravenous Magnesium Sulfate After Acute Stroke; Stroke; May 1998; 29:918-923; 7 pages.
Khaled; Role of 5-HT Receptors in Treatment of Overactive Bladder; Drugs Today (Barc). Aug. 2003; 39 (8); 599-607 (abstract only); 2 pages.
Invernizzi; Flibanserin, a Potential Antidepressant Drug, Lowers 5-HT and Raises Dopamine and Noradrenaline in the Rat Prefrontal Cortex Dialysate: Role of 5-HT1A Receptors; British Journal of Pharmacology (2003) 39, 1281-1288; 8 pages.
Nitti; Duloxetine: A New Pharmacologic Therapy for Stress Urinary Incontinence; Reviews in Urology; 2004; vol. 6 (Suppl. 3): S48-S55; 8 pages.
Rezakhaniha; Efficacy of Desmopressin in Treatment of Nocturia in Elderly Men; J Res Med Sci.; Apr. 2011; 16 (4): 516-523; 8 pages.
Mayo Clinic: Overactive Bladder, 2015; http://www.mayoclinic.org/diseases-conditions/overactive-bladder/basics/prevention/con-2; 3 pages.
Urinary Incontinence—Prevention—NHS Choices, 2014, http://www.nhs.uk/Conditions/Incontinence-urinary/Pages/Prevention.aspx.
Borsini et al.; Filbanserin: Antidepressant, 5-HT(1A) Receptor Agonist 5-HT2 Receptor Antagonist; Drugs of the Future; (1998) vol. 23, No. 1; pp. 9-16; 8 pages.

(56) References Cited

OTHER PUBLICATIONS

Dow; Using Dow Excipients for Controlled Release of Drugs in Hydrophilic Matrix Systems, 2006; pp. 1-34,36 pages.
Rueter et al.; Electrophysiological Examination of the Effects of Sustained Flibanserin Administration on Serotonin Receptors in Rat Brain; British Journal of Pharmacology 1999; 126, 627-638; 12 pages.
Steiner M: "Recognitiion of premenstrual dysphoric disorder and its treatment" Lancet the, Lancet Limited. London, GB, vol. 356, No. 9236, Sep. 30, 2000 (Sep. 30, 2000), pp. 1126-1127.
Office Action in commonly owned Canadian Patent Application No. 2,682,015; dated Dec. 20, 2013, 3 pages.
International Search Report for PCT/US00/18217 dated Oct. 26, 2000.
International Search Report for PCT/EP00/06091 dated Jan. 30, 2001.
International Search Report for PCT/US05/24623 dated Nov. 4, 2005.
International Search Report for PCT/EP02/08466 dated Nov. 21, 2002.
International Search Report for PCT/EP02/11103 dated Jan. 14, 2003.
International Search Report for PCT/EP03/02184 dated Aug. 12, 2003.
International Search Report for PCT/EP03/05226 dated Sep. 17, 2003.
Borsini et al.; Further Characterization of Potential Antidepressant Action of Flibanserin; Psychopharmacology: (2001) 159:64-69; 7 pages.
International Search Report for PCT/EP05/04081 dated Oct. 11, 2005.
International Search Report for PCT/EP05/04086 dated Oct. 11, 2005.
International Search Report for PCT/EP06/64825 dated Nov. 17, 2006.
International Search Report for PCT/EP07/57064 dated Nov. 6, 2007.
International Search Report for PCT/EP07/58301 dated Jul. 24, 2008.
International Search Report for PCT/EP07/58302 dated Jun. 4, 2008.
Office Action in counterpart Canadian Patent Application No. 2,563,743; dated Apr. 3, 2013, 2 pages.
Office Action in commonly owned Korean Patent Application No. 10-2008-7013699; dated Jun. 12, 2013, 10 pages.
Office Action in commonly owned Brazilian Patent Application No. PI0211601-4; dated Sep. 20, 2012 9 pages.
Berge et al.; Pharmaceutical Salts; Journal of Pharmaceutical Sciences; Jan. 1977; vol. 66, No. 1; pp. 1-19.
Cremers et al.; Non Erectile Dysfunction Application of Sildenafil; Herz, 2003; 28, No. 4; pp. 325-333.
Rosen et al.; The Female Sexual Function Index (FSFI): A Multidimensional Self-Report Instrument for the Assessment of Female Sexual Function; Journal of Sex & Marital Therapy, 26:191-208, 2000.
Prehn et al., Neuroprotective properties of 5-HT1A receptor agonists in rodent models of focal and global cerebral ischemia, 1991, European Journal of Pharmacology, vol. 203, pp. 213-222.
Elger et al., Oedema reduction by levernopamil in focal cerebral ischemia of spontaneously hypertensive rats studied by magnetic resonance imaging, 1994, European Journal of Pharmacology, vol. 254, pp. 65-71.
Albertazzi; Noradrenergic and serotonergic modulation to treat vasomotor symptoms; J. Br. Menopause Soc., Mar. 12, 2006; (1) 7-11; Abstract.
Ghizzani, et al.; Management of Sexual Dysfunctions in Women; J. Endorinol. Invest. 26 (Suppl to No. 3): 2003; pp. 137-138.
Lachman et al.; The Theory and Practice of Industrial Pharmacy, 3rd Edition, Lea and Febiger Philadelphia, 1986, pp. 324-333.

Response filed Aug. 24, 2012 in counterpart Brazilian Patent Application No. PI0311189-0; 13 pages [Portuguese-language only].
Response filed Sep. 6, 2012 in counterpart European Patent Application No. 07787338.8; 4 pages.
Response filed Apr. 30, 2012 in counterpart Brazilian Patent Application No. PI0211601-4; 12 pages [Portuguese-language only].
Response filed Aug. 27, 2012 in counterpart Australian Patent Application No. 2006311038; 16 pages.
Response filed Dec. 19, 2012 in counterpart European Patent Application No. 06764270.2; 26 pages.
Doelker et al., Physicochemical behavior or active substances. Consequences for the feasibility and stability of pharmaceutical forms, S.T.P. Pharma Pratiques, 1999, 9(5):399-409.
Engleson, Concise Encyclopedia Chemistry, 1993, pp. 872-873.
Clayton et al., Validation of the Decreased Sexual Desire Screener (DSDS): a Brief Diagnostic Instrument for Generalized, Acquired Hypoactive Sexual Desire Disorder in Women, International Society for the Study of Womens Sexual Health (ISSWSH) annual meeting, 2007, 2 pgs. (poster and abstract).
Clayton et al.. Validity of Sexual Distress Scales vs Electronic Diary in Women with Decreased Sexual Desire , American College of Obstetrics and Gynecologists (ACOG) annual meeting, 2007,Supplement in Obstetrics and Gynecology, 1 pg. (abstract only).
Clayton et al., Validating the Sexual Interest and Desire Inventory (SIDI-F) in North American Women , American College of Obstetrics and Gynecologists (ACOG) annual meeting, 2007, 1 pg. (abstract only).
Clayton et al., Baseline characteristics of patients enrolled in three Phase III North American trials of flibanserin in premenopausal women with Hypoactive Sexual Desire Disorder, Joint Congress of the European and International Societies of Sexual Medicine (ESSM/TSSM) 2008, 1 pgs. (abstract).
Derogatts et al., Validation of the Female Sexual Distress Scale Revised (FSDS-R) for assessing distress in women with Hypoactive Sexual Desire Disorder (HSDD), J Sex Med., 2008, 5:357-364.
Van Lundsen, Validation of the Sexual Interest and Desire Inventoy-Female (SIDI-F) in European women, ISSWSH, 2007, 2 pgs. (abstract).
Clayton et al., Baseline Characteristics of Patients Enrolled in Three Phase III North American Trials of Flibanserin in Premenopausal Women With Hypoactive Sexual Desire Disorder, FIGO 2009, Oct. 2009, 1 pg., Cape Town, South Africa. (abstract).
Flik et at., Assessment of serotonin and catecholamine levels in the female rat brain following acute and chronic administration with flibanserin, a potential novel treatment for hypoactive sexual desire disorder: An in vivo microdialysis study, presented at Neuroscience 2009, Feb. 3, 2010, http://www.abstractsonline.com/Plan/AbstractPrintView.aspx?mID=2285&sKey=65206 . . . , 2 pgs.
Banfi et al., Benzimidazolone Derivatives: a new class of putative antidepressant agents, 13th Int. Symp. on Medicinal Chemistry, Sep. 19-23, 1994, p. 102. (abstract).
Podiiorna et al., Flibanserin has anxiolytic effects without locomotor side effects in the infant rat ultrasonic vocalization model of anxiety, Workshop on Depression Anxiety Spectrum Disorders: from Neurobiology to Novel Pharm. Treatmts, Int. Acad. for Biomed. and Drug Res., Abstract-Book, Milan, Sep. 6-7, 2000, 1 pg.
Cervo et al., Involvement or 5-HT1A receptors in flibanserin discriminative stimulus in female rats, Dept. CNS Diseases, Prog. No. 465.20, 2009 Neurosci., Oct. 19, 2009, 1 pg. (poster).
Ferger et al., Neurochemical characterization of Flibanserin a phase III drug for treatment of hypoactive sexual desire disorder (HSDD) in women, Neurosci 2009, Feb. 3, 2010, http://www.abstractsonline.com/Plan/AbstractPrintView.aspx?rnIK=2285&sKey=65206 . . . , 2pgs.
Examiner's Interview dated Jun. 23, 2006, U.S. Appl. No. 10/272,603, filed Oct. 16, 2002 now U.S. Pat. No. 7,151,303, issued Dec. 19, 2006, 2 pgs.
Kumar et al., An Overview of Automated Systems Relevant in Pharmaceutical Salt Screening; Drug Discovery Today, 2007, 12(23-24):1046-1053.
Stahl et al., Handbook of Pharmaceutical Salts: Selection and Use, Helvetica Chim. Acta, 2002, pp. 1-7.

(56) References Cited

OTHER PUBLICATIONS

Nappi et al., Efficacy of Flibanscrin as a Potential Treatment for Hypoactive Sexual Desire Disorder in European Premenopausal Women: Results From the Orchid Trial; ESSM 2009, Nov. 2009, 1 pg., Lyon. (abstract).
Holstege et al., Brain activation and de-activation caused by erotic movies is lower in HSDD- than in non-HSDD volunteers, ESSM 2009, 8 pgs. (oral presentation).
Jolly et al., Safety and Tolerability of Flibanserin in Premenopausal Women With Hypoactive Sexual Desire Disorder, ESSM 2009, Nov. 2009, 1 pg., Lyon. (abstract).
Fuchs, Baseline Characteristics of Patients Enrolled in Three Phase III North American Trials of Flibanserin in Premenopausal Women With Hypoactive Sexual Desire Disorder, FIGO 2009, Oct. 2009, 10 pgs., Cape Town, South Africa. (oral presentation).
Goldfischer, Efficacy and Safely of Flibanserin in a Randomized Withdrawal Study of Premenopausal Women With Hypoactive Sexual Desire Disorder, FIGO2009, Oct. 2009, 12 pgs., Cape Town, South Africa. (oral presentation).
Rosen et al., Criterion Validity of the Sexual Desire Domain of the Female Sexual Function Index (Fsfi): Identifying a Diagnostic Cut-Point for Differentiating Women With and Without Hsdd, ICSM 2009, Jul. 2009, 2 pgs., Paris. (poster and abstract).
Jayne et al., Results Front the Dahlia (511.70) Trial: A Prospective Study of Flibanserin for the Treatment of Hypoactive Sexual Desire Disorder in North American Premenopausal Women, SMSNA 2009, Nov. 2009, 2 pgs., San Diego, USA (abstract and poster).
Sand et al., The Female Sexual Function Index (Fsfi) is a Potential "Gold Standard" Measure for Assessing Sexual Function in Pre- and Post-Menopausal Women: A Systematic Review, SMSNA 2009, Nov. 2009, 2 pgs., San Diego, USA. (poster and abstract).
Sand, Efficacy of Flibanserin 100 Mg Qhs as a Potential Treatment for Hypoactive Sexual Desire Disorder in North American Pre-menopausal Women, SMSNA 2009, Nov. 2009, 2 pgs., San Diego, USA. (oral presentation).
Holstege et al., Differences in Brain Activity in Premenopausal Women With Hypoactive Sexual Desire Disorder (IIsdd) Compared to Women Without Sexual Dysfunction, SMSNA 2009, Nov. 2009, 2 pgs., San Diego, USA (abstract only).
Holstege et al., Brain activation and de-activation caused by erotic movies is lower in HSDD- than in non-HSDD volunteers, SMSNA, 2009, 4 pgs (poster & oral presentation).
Sand et al., Pooled Clinical Trail Analysis of Flibanserin Safety and Tolerability in Premenopausal Women with Hypoactive Sexual Desire Disorder, SMSNA, 2009, 2 pgs. (poster and abstract).
Sand, Pooled Clinical Trail Analysis of Flibanscrin Safety and Tolerability in Premenopausal Women with Hypoactive Sexual Desire Disorder, SMSNA, 2009, 2 pgs. (oral presentation).
Sand et al., Effacacy of Plibanserin in North American Premeno-pausal Women with Hypoactive Sexual Desire Disorder: Results from the Violet Trial, SMSNA, 2009, 3 pgs. (poster and abstract).
Goldfischer, Efficacy and Safety of Flibanserin in a Randomized Withdrawal Study of Premenopausal Women With Hypoactive Sexual Desire Disorder, WAS, 2009, 12 pgs. (oral presentation).
Clayton et al., Baseline Characteristics of Patients Enrolled in Three Phase III North American Trials of Flibanserin in Premenopausaul Women with Hypoactive Sexual Desire Disorder, WAS, 2009, 2 pgs. (poster and abstract).
Clayton, Baseline Characteristics of Patients Enrolled in Three Phase III North American Trials of Flibanscrin in Premenopausaul Women with Hypoactive Sexual Desire Disorder, WAS, 2009, 4 pgs. (oral presentation).
Lewis-D' Agostino et al., Validating the Sexual Interest and Desire Inventory (SIDI-P) in North American Women , American College of Obstetrics and Gynecologists (ACOG) annual meeting, 2007, 1 pg. (poster).
Office Action dated Jul. 9, 2008, Ussn 11/278551 filed Apr. 4, 2006, 12 pgs.

Shibata, et al., "Ischemia-induced impairment of 2-deoxyglucose uptake and CA1 field potentials in rat hippocampal slices: protection by 5-$HT_{1A}$ receptor agonists and 5-$HT_2$ receptor antagonists," European Journal of Pharmacology, 229 (1992) 21-29.
"Types of Back Pain: Acute Pain, Chronic Pain, and Neuropathic Pain," Spine-health.com, www.spine-health.com/topics/cd/chronicpain02.html, (Oct. 2, 2007).
U.S. Appl. No. 11/956,949, filed Dec. 4, 2007, D. Lewis-D'Agostino et al.
Konarski et al., "Effects of Acute Flibanserin on FDG-PET Brain Glucose Metabolism in Men with Major Depressive Disorder," Aug. 2008 (poster).
Konarski et al., "Effects of Acute Flibanserin on FDG-PET Brain Glucose Metabolism in Men with Major Depressive Disorder," Aug. 2008 Barcelona meeting of the European College of Nueropsychopharmacology (abstract).
Cools, A. R. "Depression and Psychosis" Behavioural Pharmacology of 5-HT, pp. 153-155 (1989).
Archer, T. "SHT, Pain and Anxiety" Behavioural Pharmacology of 5-HT, p. 299-300 (1989).
Cloninger, C. R. "A Systematic Method for Clinical Description and Classification of Personality Variants" Arch. Gen. Psychiatry, vol. 44, pp. 573-588 (Jun. 1987).
Reikkinen et al. "The Effects of Increased Serotonergic and Decreased Cholinergic Activities on Spatial Navigation Performance in Rats" Pharmacology Biochemistry & Behavior, vol. 39, pp. 25-29 (1991).
Crook, T. and Lakin, M. "Effects of Ondansetron in Age-associated Memory Impairment" The role of ondansetron, a novel 5-HT3 antagonist, in the treatment of psychiatric disorders, 5th World Congress of Biochemical Psychiatry, pp. 21-23 (1991).
Darlington, C. "Flibanserin" Current Opinion in CPNS Investigational Drugs, 1999 1(4): 510-513.
Borsini et al. Behavioral Effects of Flibanserin (BIMT-l7), Sep. 1999, Pharmacology, Biochemistry and Behavior, vol. 64, issue 1, see abstract.
Borsini, F. et al. "BIMT-17, a 5HT-2A receptor antagonist and 5HT-1A receptor full agonist in rat cerebral cortex" Naunyn-Schmiedeberg's Archives of Pharm., 352(3) 1995, pp. 276-282.
Giron, D. "Thermal analysis and calorimetric methods in the characeterization of polymorphs and solvates" Thermochimica ACTA, Elsevier Science, 248, 1995, pp. 1-59.
Borsini et al., Flibanserin, Drugs of the Future, 1998, 23(1):9-16.
Jean L. Fourcroy "Female Sexual Dysfunction: Potential for Pharmacotherapy" Drugs 2003, vol. 63, No. 14, pp. 1445-1457.
Greene, T. "Protective Groups in Organic Synthesis", Havard University, pp. 10-17, 1981 (Wiley-Interscience Publication).
Chemical Abstract: Database Accession No. 98:16650-XP002197885
Collino, F. et al.: Mannich bases of benzimidazoles, benzotriazoles and other analogous compounds, with Pharmacological activity.
Chalmers et al., "Corticotrophin-releasing factor receptors: from molecular biology to drug design", TiPS vol. 17, pp. 166-172, Apr. 1996.
Lyrer, "Neue Ansatze in der Akutbehandlung des zerebrovaskularen Insultes" Schweiz. Med. Wochenschr., vol. 124, #45, 2005-2012 1994.
Damour et al. CA 118-124537e (1992).
Awouters et al. CA 88-98788 (1977).
Vaudenberk et al. CA 88-50920n (1977).
Invernizzi et al., "Flibanserin, a potential antidepressant drug, lowers 5-HT and raises dopamine and noradrenaline in the rat prefrontal cortex dialysate: role of 5-$HT_{1A}$ receptors", British Journal of Pharmacology, vol. 139, vol. 1281-1288, Jun. 2003.
Rueter, L. E. et al.; "Electrophysiological examination of the effects of sustained flibanserin administration on serotonin receptors in rat brain"; British J of Pharm, 1999, vol. 126, No. 3, pp. 627-638.
"Flibanserin has anxiolytic effects without locomotor side effects in the infant rat ultrasonic vocalization model of anxiety", Podhorna et al., abstract, British Journal of Pharmacology, 2000, vol. 130, No. 4, pp. 739-746.

TREATING SEXUAL DESIRE DISORDERS WITH FLIBANSERIN

CROSS-REFERENCE TO RELATED APPLICATIONS

The present application is a continuation of U.S. patent application Ser. No. 16/125,883, filed Sep. 10, 2018, which is a continuation of U.S. patent application Ser. No. 15/694, 317, filed Sep. 1, 2017 (Now U.S. Pat. No. 10,098,876), which is a continuation of U.S. patent application Ser. No. 15/270,167, filed Sep. 20, 2016 (Now U.S. Pat. No. 9,782, 403), which is a continuation of U.S. patent application Ser. No. 14/640,055, filed Mar. 6, 2015 (Now U.S. Pat. No. 9,468,639), which is a continuation of U.S. patent application Ser. No. 14/269,373, filed May 5, 2014, which is a continuation of U.S. patent application Ser. No. 13/920,354, filed Jun. 18, 2013, which is a continuation of U.S. patent application Ser. No. 13/551,036, filed Jul. 17, 2012, which is a continuation of U.S. patent application Ser. No. 11/524, 268, filed Sep. 21, 2006 (Now U.S. Pat. No. 8,227,471), which is a continuation of U.S. patent application Ser. No. 10/272,603, filed Oct. 16, 2002 (Now U.S. Pat. No. 7,151, 103), which claims priority to U.S. Provisional Patent Application No. 60/348,911, filed Oct. 23, 2001 and European Patent Application No. EP 01 1250 20.6, filed Oct. 20, 2001, the disclosures of each of which are incorporated herein by reference in their entireties.

FIELD OF THE INVENTION

The invention relates to the use of flibartserin for the preparation of a medicament for the treatment of disorders of sexual desire.

BACKGROUND OF THE INVENTION

The compound 1-[2-(4-(3-trifluoromethyl-phenyl)piperazin-1-yl)ethyl]-2,3-dihydro-1H-benzimidazol-2-one (flibanserin) is disclosed in form of its hydrochloride in European Patent Application EP-A-526434 and has the following chemical structure.

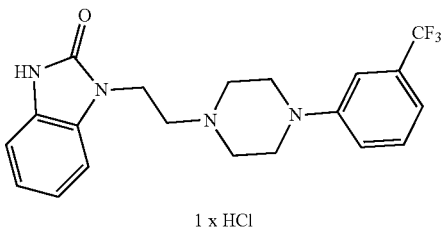 [SMILES: O=c1[nH]c2ccccc2n1CCN1CCN(c2cccc(C(F)(F)F)c2)CC1]

1 x HCl

Flibanserin shows affinity for the 5-HT1A and 5-HT2-receptor. It is therefore a promising therapeutic agent for the treatment of a variety of diseases, for instance depression, schizophrenia, and anxiety.

DETAILED DESCRIPTION OF THE INVENTION

In studies of male and female patients suffering from sexual dysfunction it has been found that flibanserin optionally in form of the pharmacologically acceptable acid addition salts thereof displays sexual desire enhancing properties. Accordingly, the instant invention relates to the use of flibanserin, optionally in of the pharmacologically acceptable acid addition salts thereof for the preparation of a medicament for the treatment of disorders of sexual desire.

In a preferred embodiment the invention relates to the use of flibanserin, optionally in form of the pharmacologically acceptable acid addition salts thereof for the preparation of a medicament for the treatment of disorders selected from the group consisting of Hypoactive Sexual Desire Disorder, loss of sexual desire, lack of sexual desire, decreased sexual desire, inhibited sexual desire, loss of libido, libido disturbance, and frigidity.

Particular preferred according to the invention is the use of flibanserin, optionally in form of the pharmacologically acceptable acid addition salts thereof for the preparation of a medicament for the treatment of disorders selected from the group consisting of Hypoactive Sexual Desire Disorder, loss of sexual desire, lack of sexual desire, decreased sexual desire, inhibited sexual desire.

In a particularly preferred embodiment the invention relates to the use of flibanserin, optionally in form of the pharmacologically acceptable acid addition salts thereof for the preparation of a medicament for the treatment of disorders selected from the group of Hypoactive Sexual Desire Disorder and loss of sexual desire.

The observed effects of flibanserin can be achieved in men and women. However, according to a further aspect of the invention the use of flibanserin optionally in form of the pharmacologically acceptable acid addition salts thereof for the preparation of a medicament for the treatment of female sexual dysfunction is preferred.

The beneficial effects of flibanserin can be observed regardless of whether the disturbance existed lifelong or was acquired, and independent of etiologic origin (organic—both, physically and drug induced—, psychogen, a combination of organic—both, physically and drug induced—, and psychogen, or unknown).

Flibanserin con optionally used in form of its pharmaceutically acceptable acid addition salts. Suitable acid addition salts include for example those of the acids selected from, succinic acid, hydrobromic acid, acetic acid, fumaric acid, maleic acid, methanesulphonic acid, lactic acid, phosphoric acid, hydrochloric acid, sulphuric acid, tartaric acid and citric acid. Mixtures of the abovementioned acid addition salts may also be used. From the aforementioned acid addition salts the hydrochloride and the hydrobromide, particularity the hydrochloride, are preferred.

Flibanserin, optionally used in form of its pharmaceutically acceptable acid addition salts, may be incorporated into the conventional pharmaceutical preparation in solid, liquid or spray form. The composition may, for example, be presented in a form suitable for oral, rectal, parenteral administration or for nasal inhalation: preferred forms includes for example, capsules, tablets, coated tablets, ampoules, suppositories and nasal spray. The active ingredient may be incorporated in excipients or carriers conventionally used in pharmaceutical compositions such as, for example, talc, arabic gum, lactose, gelatine, magnesium stearate, corn starch, acqueous or non acqueous vehicles, polyvynil pyrrolidone, semisynthetic glicerides of fatty acids, benzalconium chloride, sodium phosphate, EDTA, polysorbate 80. The compositions are advantageously formulated in dosage units, each dosage unit being adapted to supply a single dose of the active ingredient. The dosis range applicable per day is between 0.1 to 400, preferably between 1.0 to 300, more preferably between 2 to 200 mg.

Each dosage unit may conveniently contain from 0.01 mg to 100 mg, preferably from 0.1 to 50 mg.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g of a flavouring such as vanilline or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g of with the addition of preservatives such as p-hydroxybenzoates, or stabilisers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

The Examples which follow illustrate the present invention without restricting its scope:

Examples of Pharmaceutical Formulations

| A) | Tablets | per tablet |
|---|---|---|
| | flibanserin hydrochloride | 100 mg |
| | lactose | 240 mg |
| | corn starch | 340 mg |
| | polyvinylpyrrolidone | 45 mg |
| | magnesium stearate | 15 mg |
| | | 740 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | flibanserin hydrochloride | 80 mg |
| | corn starch | 190 mg |
| | lactose | 55 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodium carboxymethyl starch and the magnesium stearate are added and mixed in and the mixture is compressed to form tablets of a suitable size.

| C) | Coated tablets | per coated tablet |
|---|---|---|
| | flibanserin hydrochloride | 5 mg |
| | corn starch | 41.5 mg |
| | lactose | 30 mg |
| | polyvinylpyrrolidone | 3 mg |
| | magnesium stearate | 0.5 mg |
| | | 80 mg |

The active substance, corn starch, lactose and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D) | Capsules | per capsule |
|---|---|---|
| | flibanserin hydrochloride | 1 50 mg |
| | Corn starch | 268.5 mg |
| | Magnesium stearate | 1.5 mg |
| | | 420 mg |

The substance and corn starch are mixed and moistened with water. The moist mass is screened and dried. The dry granules are screened and mixed with magnesium stearate. The finished mixture is packed into size 1 hard gelatine capsules.

| E) | Ampoule solution | |
|---|---|---|
| | flibanserin hydrochloride | 50 mg |
| | sodium chloride | 50 mg |
| | water for inj. | 5 ml |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion.

| F) | Suppositories | |
|---|---|---|
| | flibanserin hydrochloride | 50 mg |
| | solid fat | 1650 mg |
| | | 1700 mg |

The hard fat is melted. At 40° C. the ground active substance is homogeneously dispersed. It is cooled to 3° C. and poured into slightly chilled suppository moulds.

The invention claimed is:

1. A method of treating a female hypoactive sexual desire disorder in a human adult patient, comprising orally administering a therapeutically effective amount of flibanserin to the patient to treat the female hypoactive sexual desire disorder.

2. The method according to claim 1, wherein the amount administered is between about 0.1 mg and 400 mg per day of flibanserin.

3. The method according to claim 1, wherein the amount administered is between about 1 mg and 300 mg per day of flibanserin.

4. The method according to claim 1, wherein the amount administered is in a dosage unit containing between about 0.01 mg and 100 mg of flibanserin.

5. The method according to claim 1, wherein the amount administered is in a dosage unit containing about 100 mg.

6. A method of treating a female hypoactive sexual desire disorder in a human adult patient, comprising orally administering a tablet comprising a therapeutically effective amount of flibanserin to the patient to treat the female hypoactive sexual desire disorder.

7. The method according to claim 6, wherein the amount administered is between about 0.1 mg and 400 mg per day of flibanserin.

8. The method according to claim 6, wherein the tablet comprises about 0.01 mg to 100 mg of flibanserin.

9. The method according to claim 6, wherein the tablet comprises about 100 mg flibanserin.

10. The method according to claim 6, wherein the tablet further comprises one or more excipients or carriers.

11. The method according to claim 10, wherein the one or more excipients or carriers comprise at least one inert diluent.

12. The method according to claim 11, wherein the at least one inert diluent is selected from calcium carbonate, calcium phosphate, lactose, and combinations thereof.

13. The method according to claim 10, wherein the one or more excipients or carriers comprise at least one lubricant.

14. The method according to claim 13, wherein the at least one lubricant is selected from the group consisting of magnesium stearate, talc, and combinations thereof.

15. The method according to claim 10, wherein the one or more excipients or carriers comprise at least one distintegrant.

16. The method according to claim 15, wherein the at least one disintegrant is selected from corn starch, alginic acid, and combinations thereof.

17. The method according to claim 10, wherein the one or more excipients or carriers comprise at least one binder.

18. The method according to claim 17, wherein the at least one binder is selected from starch, gelatin, and combinations thereof.

19. The method according to claim 10, wherein the one or more excipients or carriers comprise at least one agent for delaying release.

20. The method according to claim 19, wherein the at least one agent for delaying release is selected from carboxymethyl cellulose, cellulose acetate phthalate, polyvinyl acetate, and combinations thereof.

21. The method according to claim 6, wherein the tablet further comprises one or more sweeteners, one or more flavor enhancers, preservatives, or a combination thereof.

22. The method according to claim 6, wherein the tablet further comprises magnesium stearate, talc, and microcrystalline cellulose.

23. The method according to claim 22, wherein the tablet further comprises one or both of lactose and sodium-carboxymethyl starch.

24. The method according to claim 10, wherein the tablet comprises a compressed mixture of flibanserin and the one or more excipients or carriers.

25. The method according to claim 6, wherein the tablet is uncoated.

* * * * *